US012210009B2

(12) United States Patent
Goltzman et al.

(10) Patent No.: US 12,210,009 B2
(45) Date of Patent: Jan. 28, 2025

(54) ON-VEHICLE WATER IN FUEL SENSING SYSTEM AND RELATED SIGNAL PROCESSING

(71) Applicant: Donaldson Company, Inc., Minneapolis, MN (US)

(72) Inventors: Chad M. Goltzman, Bloomington, MN (US); Davis B. Moravec, Burnsville, MN (US); Mikayla A. Yoder, Eagan, MN (US); Michael J. Cronin, Apple Valley, MN (US); Sterling C. Hansen, Richfield, MN (US); Bradly G. Hauser, Minneapolis, MN (US); David D. Lauer, Minneapolis, MN (US); Danny W. Miller, Ackley, IA (US)

(73) Assignee: Donaldson Company, Inc., Bloomington, MN (US)

( * ) Notice: Subject to any disclaimer, the term of this patent is extended or adjusted under 35 U.S.C. 154(b) by 158 days.

(21) Appl. No.: 17/496,385

(22) Filed: Oct. 7, 2021

(65) Prior Publication Data
US 2022/0107303 A1    Apr. 7, 2022

Related U.S. Application Data

(60) Provisional application No. 63/088,767, filed on Oct. 7, 2020.

(51) Int. Cl.
*G01N 33/28*   (2006.01)
*F02M 37/26*   (2019.01)
(Continued)

(52) U.S. Cl.
CPC ......... *G01N 33/2847* (2013.01); *F02M 37/26* (2019.01); *G01F 1/74* (2013.01);
(Continued)

(58) Field of Classification Search
CPC .... G01N 33/2847; G01N 21/59; B60K 15/03; B60K 2015/0321; G01F 1/74
(Continued)

(56) References Cited

U.S. PATENT DOCUMENTS

| 4,638,305 A | 1/1987 | Sutton |
| 5,033,858 A * | 7/1991 | Twerdochlib .......... G01N 15/06 356/335 |

(Continued)

FOREIGN PATENT DOCUMENTS

| CN | 101715545 | 5/2010 |
| CN | 101965447 | 2/2011 |

(Continued)

OTHER PUBLICATIONS

"Elveflow Microfluidic Bubble Detector Product Information," from Elveflow 2021 Product Catalog. Accessible at URL <elveflow.com/microfluidic-flow-control-products/microfluidic-flow-control-module/microfluidic-liquid-sensor/> (2 pages).

(Continued)

*Primary Examiner* — Michelle M Iacoletti
*Assistant Examiner* — Noah J. Haney
(74) *Attorney, Agent, or Firm* — Pauly, DeVries Smith & Deffner LLC

(57) ABSTRACT

Embodiments herein relate to water in fuel sensing systems that can be mounted on-vehicle. In an embodiment, a water in fuel sensing system is included having a light source, a light detector, and a sensor controller, wherein the sensor controller is in signal communication with the light detector and the sensor controller is configured to evaluate signals received from the light detector, identify water droplets based on the signals received from the light detector, record information regarding the classified water droplets, and (Continued)

generate an estimate of an amount of water in a fuel. Other embodiments are also included herein.

19 Claims, 24 Drawing Sheets

(51) Int. Cl.
 G01F 1/74 (2006.01)
 G01N 21/17 (2006.01)
 G01N 21/31 (2006.01)
 G01N 21/59 (2006.01)
(52) U.S. Cl.
 CPC .............. *G01N 21/17* (2013.01); *G01N 21/31* (2013.01); *G01N 21/59* (2013.01); *G01N 2021/1736* (2013.01)
(58) Field of Classification Search
 USPC ........................................................ 356/436
 See application file for complete search history.

(56) References Cited

U.S. PATENT DOCUMENTS

| | | | |
|---|---|---|---|
| 5,078,901 A | 1/1992 | Sparrow | |
| 5,388,629 A | 2/1995 | Kami | |
| 5,880,674 A | 3/1999 | Ufkes et al. | |
| 6,260,004 B1 | 7/2001 | Hays et al. | |
| 8,461,519 B2 | 6/2013 | Lievois et al. | |
| 8,473,185 B2 | 6/2013 | Suwa et al. | |
| 8,781,673 B2* | 7/2014 | Nunn | F02D 41/0025 702/50 |
| 8,873,060 B2* | 10/2014 | Webb | G01N 21/84 385/12 |
| 9,518,913 B2 | 12/2016 | Wilhelm | |
| 11,131,627 B2* | 9/2021 | Bachalo | G01N 15/0227 |
| 2003/0085180 A1 | 5/2003 | Akins et al. | |
| 2008/0121026 A1* | 5/2008 | Verdegan | G01N 15/0205 702/22 |
| 2008/0237503 A1* | 10/2008 | Albertson | G01N 33/2847 250/564 |
| 2009/0038406 A1 | 2/2009 | Hocker | |
| 2009/0050809 A1* | 2/2009 | Holec | G01F 1/74 250/343 |
| 2009/0101822 A1* | 4/2009 | Mitra | G01N 21/534 356/73 |
| 2009/0241672 A1 | 10/2009 | Gysling | |
| 2010/0134304 A1 | 6/2010 | Weinstein et al. | |
| 2012/0027630 A1 | 2/2012 | Forsberg et al. | |
| 2012/0046848 A1 | 2/2012 | Suwa et al. | |
| 2012/0223515 A1* | 9/2012 | Avramescu | G01N 33/2847 280/830 |
| 2012/0312530 A1* | 12/2012 | Pope | E21B 49/087 250/269.1 |
| 2014/0047827 A1 | 2/2014 | Maoued et al. | |
| 2014/0216602 A1 | 8/2014 | Kastner et al. | |
| 2014/0268156 A1* | 9/2014 | Smythe | G01N 21/59 356/436 |
| 2014/0331742 A1 | 11/2014 | Campbell et al. | |
| 2015/0021482 A1* | 1/2015 | Muller | G01N 21/8914 250/341.1 |
| 2015/0276589 A1 | 10/2015 | Wagner et al. | |
| 2016/0011100 A1* | 1/2016 | Cipullo | G01N 21/8507 356/436 |
| 2016/0258870 A1 | 9/2016 | Tokhtuev et al. | |
| 2017/0329355 A1* | 11/2017 | Kanade | F02M 37/0076 |
| 2017/0356838 A1* | 12/2017 | Knollenberg | G01F 1/704 |
| 2019/0242814 A1* | 8/2019 | Bachalo | G01N 21/85 |
| 2020/0400544 A1 | 12/2020 | Etschmaier et al. | |
| 2020/0400559 A1* | 12/2020 | Martensson | G01N 1/14 |
| 2021/0223154 A1 | 7/2021 | Moravec et al. | |
| 2021/0310942 A1* | 10/2021 | Jones | G01N 21/314 |
| 2023/0296529 A1 | 9/2023 | Moravec et al. | |

FOREIGN PATENT DOCUMENTS

| | | | |
|---|---|---|---|
| CN | 103576640 | 2/2014 | |
| CN | 108374695 | 8/2018 | |
| CN | 107807402 | 8/2020 | |
| EP | 2869057 | 5/2015 | |
| EP | 3745096 | 12/2020 | |
| GB | 2568089 | 5/2019 | |
| JP | S60161546 | 8/1985 | |
| JP | 2010053691 | 3/2010 | |
| JP | 2010053691 A * | 3/2010 | ............ F02D 45/00 |
| JP | 2010528319 | 8/2010 | |
| JP | 2017223672 | 12/2017 | |
| KR | 20060041569 | 5/2006 | |
| KR | 20230133468 | 9/2023 | |
| WO | 2008147408 | 12/2008 | |
| WO | 2010111231 | 9/2010 | |
| WO | 2019108731 | 6/2019 | |
| WO | 2019232305 | 12/2019 | |
| WO | 2021003346 | 1/2021 | |
| WO | 2022076747 | 4/2022 | |
| WO | 2023177728 | 9/2023 | |

OTHER PUBLICATIONS

"International Preliminary Report on Patentability," for PCT Application No. PCT/US2020/040625 mailed Jan. 13, 2022 (9 pages).
"International Search Report and Written Opinion," for PCT Application No. PCT/US2020/040625 mailed Oct. 26, 2020 (13 pages).
"International Search Report and Written Opinion," for PCT Application No. PCT/US2021/054055 mailed Mar. 14, 2022 (21 pages).
"First Office Action," for Chinese Patent Application No. 202080045491.5 mailed Aug. 11, 2023 (30 pages) with English Translation.
"International Preliminary Report on Patentability," for PCT Application No. PCT/US2021/054055 mailed Apr. 20, 2023 (15 pages).
"International Search Report and Written Opinion," for PCT Application No. PCT/US2023/015280 mailed Jul. 14, 2023 (13 pages).
"Response to Communication Pursuant to Rules 161(1) and 162 EPC," for European Patent Application No. 20757982.2 filed Aug. 16, 2022 (34 pages).
"Non-Final Office Action," for U.S. Appl. No. 17/621,617 mailed Jan. 31, 2024 (28 pages).
"Non-Final Office Action," for Japanese Patent Application No. 2021-571466 mailed Mar. 1, 2024 (7 pages).
"Response to Non Final Office Action," for U.S. Appl. No. 17/621,617 filed on Apr. 29, 2024 (10 pages).
"Second Office Action," for Chinese Patent Application No. 202080045491.5 mailed Mar. 2, 2024 (20 pages) with English Translation.
"Aeration," Minnesota Rural Water Association, https://www.mrwa.com/WaterWorksMnl/Chapter%2011%20Aeration.pdf (Year: 2011).
"Cavitation," ScienceDirect, https://www.sciencedirect.com/topics/chemistry/cavitation (Year: 2019).
"Final Office Action," for Chinese Patent Application No. 202080045491.5 mailed Jul. 4, 2024 (27 pages) with English translation.
"Final Office Action," for U.S. Appl. No. 17/621,617 mailed Aug. 8, 2024 (27 pages).
"International Preliminary Report on Patentability," for PCT Patent Application No. PCT/US2023/015280 mailed Sep. 26, 2024 (9 pages).
"Vapor," Merriam Webster, https://www.merriam-webster.com/dictionary/vapor (Year: 2024).
"Non-Final Office Action," for U.S. Appl. No. 18/115,464 mailed Dec. 3, 2024 (23 pages).
"Office Action," for Japanese Patent Application No. 2021-571466 mailed Oct. 4, 2024 (8 pages) with English translation.

* cited by examiner

ON-VEHICLE WATER IN FUEL SENSING SYSTEM AND RELATED SIGNAL PROCESSING

This application claims the benefit of U.S. Provisional Application No. 63/088,767, filed Oct. 7, 2020, the content of which is herein incorporated by reference in its entirety.

FIELD

Embodiments herein relate to water in fuel sensing systems. More specifically, embodiments herein relate to water in fuel sensing systems that can be mounted on-vehicle.

BACKGROUND

Contaminated fuel can lead to vehicle downtime and costly repairs, especially to expensive common rail systems and components. Modern engines increasingly require better fuel filtration technology to ensure that the cleanest fuel is delivered to the vehicle's fuel system.

One contaminant in fuel is water. Water in fuel causes corrosion and will erode injector nozzles. It can negatively affect the combustion process, reduce the lubricity of the fuel and consequently damage system components. Water enters fuel from, amongst other things, storage tanks and from condensation caused by cooling temperatures.

SUMMARY

Embodiments herein relate to water in fuel sensing systems that can be mounted on-vehicle. In a first aspect, a water in fuel sensing system is included having a light source, a light detector, and a sensor controller, wherein the sensor controller is in signal communication with the light detector and the sensor controller is configured to evaluate signals received from the light detector, identify water droplets based on the signals received from the light detector, record information regarding the classified water droplets, and generate an estimate of an amount of water in a fuel.

In a second aspect, in addition to one or more of the preceding or following aspects, or in the alternative to some aspects, the sensor controller is configured to identify water droplets based on a deviation in the signals received from the light detector from a baseline level.

In a third aspect, in addition to one or more of the preceding or following aspects, or in the alternative to some aspects, the system is configured to be mounted on a vehicle.

In a fourth aspect, in addition to one or more of the preceding or following aspects, or in the alternative to some aspects, the sensor controller is configured to send information regarding the identified water droplets to a vehicular data network.

In a fifth aspect, in addition to one or more of the preceding or following aspects, or in the alternative to some aspects, the vehicular data network includes a CANBUS network.

In a sixth aspect, in addition to one or more of the preceding or following aspects, or in the alternative to some aspects, the sensor controller is configured to generate the estimate of the amount of water in the fuel based on a number of identified water droplets per unit time.

In a seventh aspect, in addition to one or more of the preceding or following aspects, or in the alternative to some aspects, the sensor controller is configured to estimate a size of identified water droplets.

In an eighth aspect, in addition to one or more of the preceding or following aspects, or in the alternative to some aspects, the sensor controller is configured to generate the estimate of the amount of water in the fuel based on a number of identified water droplets per unit time and estimated sizes of the identified water droplets.

In a ninth aspect, in addition to one or more of the preceding or following aspects, or in the alternative to some aspects, the system can further include at least one of a flow rate sensor and a differential pressure sensor.

In a tenth aspect, in addition to one or more of the preceding or following aspects, or in the alternative to some aspects, the sensor controller is configured to generate the estimate of the amount of water in the fuel based on a number of identified water droplets per unit time and a flow rate as provided by the flow rate sensor.

In an eleventh aspect, in addition to one or more of the preceding or following aspects, or in the alternative to some aspects, the sensor controller is configured to generate the estimate of the amount of water in the fuel based on a number of identified water droplets per unit time and a flow rate as received from a separate source.

In a twelfth aspect, in addition to one or more of the preceding or following aspects, or in the alternative to some aspects, the sensor controller is configured to output a signal regarding the estimated amount of free water.

In a thirteenth aspect, in addition to one or more of the preceding or following aspects, or in the alternative to some aspects, a sensor controller output signal distinguishes between acute and chronic levels of water in fuel.

In a fourteenth aspect, in addition to one or more of the preceding or following aspects, or in the alternative to some aspects, a sensor controller output signal distinguishes between a level of water creating a need to stop immediately versus a level of water allowing continued operation.

In a fifteenth aspect, in addition to one or more of the preceding or following aspects, or in the alternative to some aspects, the light source is mounted along a fuel line.

In a sixteenth aspect, in addition to one or more of the preceding or following aspects, or in the alternative to some aspects, the light source is mounted upstream from a fuel filter.

In a seventeenth aspect, in addition to one or more of the preceding or following aspects, or in the alternative to some aspects, the light source is mounted downstream from a fuel filter.

In an eighteenth aspect, in addition to one or more of the preceding or following aspects, or in the alternative to some aspects, the light source is mounted on or in a fuel filter head.

In a nineteenth aspect, in addition to one or more of the preceding or following aspects, or in the alternative to some aspects, the system further can include a flow channel, wherein the flow channel is in fluid communication with a fuel line of a vehicle.

In a twentieth aspect, in addition to one or more of the preceding or following aspects, or in the alternative to some aspects, the light source is configured to emit light into the flow channel.

In a twenty-first aspect, in addition to one or more of the preceding or following aspects, or in the alternative to some aspects, the system is configured to identify a size distribution of water droplets based on the signals received from the light detector.

In a twenty-second aspect, in addition to one or more of the preceding or following aspects, or in the alternative to some aspects, the system can include a temperature sensor, wherein the sensor controller can be further configured to evaluate signals from the temperature sensor and normalize the signals received from the light detector based on the signals from the temperature sensor.

In a twenty-third aspect, a water contamination monitoring system for a vehicle can be included herein having a light source, a light detector, and a sensor controller, wherein the sensor controller can be in electronic communication with the light detector and the sensor controller can be configured to evaluate signals received from the light detector, detect water droplets based a deviation from a baseline value, estimate water droplet size based on evaluating both any rise in the signals received from the light detector above a baseline value and any fall in the signals received from the light detector below the baseline value, and record information regarding the detected water droplets.

In a twenty-fourth aspect, in addition to one or more of the preceding or following aspects, or in the alternative to some aspects, the sensor controller can be configured to estimate droplet size based on whether a detected rise in the signals received from the light detector can be observed before a detected fall in the signals received from the light detector.

In a twenty-fifth aspect, in addition to one or more of the preceding or following aspects, or in the alternative to some aspects, the sensor controller can be configured to generate an estimate of an amount of water in a vehicular fuel.

In a twenty-sixth aspect, in addition to one or more of the preceding or following aspects, or in the alternative to some aspects, the sensor controller can be configured to save generated estimates of the amount of water in vehicular fuel along with corresponding geolocation data.

In a twenty-seventh aspect, in addition to one or more of the preceding or following aspects, or in the alternative to some aspects, the sensor controller can be configured to initiate a notification if the estimate of the amount of free water exceeds a threshold value.

In a twenty-eighth aspect, in addition to one or more of the preceding or following aspects, or in the alternative to some aspects, the threshold value can be 200 parts per million water.

In a twenty-ninth aspect, in addition to one or more of the preceding or following aspects, or in the alternative to some aspects, the sensor controller can be configured to initiate a vehicle shutdown signal if the estimate of the amount of water exceeds a threshold value.

In a thirtieth aspect, in addition to one or more of the preceding or following aspects, or in the alternative to some aspects, the sensor controller can be configured to initiate a first notification if the estimate of the amount of free water exceeds a first threshold value and initiate a second notification if the estimate of the amount of free water exceeds a second threshold value.

In a thirty-first aspect, in addition to one or more of the preceding or following aspects, or in the alternative to some aspects, the sensor controller can be configured to send information regarding the detected water droplets to a CAN-BUS network.

In a thirty-second aspect, in addition to one or more of the preceding or following aspects, or in the alternative to some aspects, the light source can be mounted along a fuel line.

In a thirty-third aspect, in addition to one or more of the preceding or following aspects, or in the alternative to some aspects, the light source can be mounted upstream from a fuel filter.

In a thirty-fourth aspect, in addition to one or more of the preceding or following aspects, or in the alternative to some aspects, the light source can be mounted downstream from a fuel filter.

In a thirty-fifth aspect, in addition to one or more of the preceding or following aspects, or in the alternative to some aspects, the light source can be mounted on or in a fuel filter head.

In a thirty-sixth aspect, in addition to one or more of the preceding or following aspects, or in the alternative to some aspects, the system further can include a flow channel, wherein the flow channel can be in fluid communication with a fuel line of a vehicle.

In a thirty-seventh aspect, in addition to one or more of the preceding or following aspects, or in the alternative to some aspects, the light source can be mounted along the flow channel.

In a thirty-eighth aspect, in addition to one or more of the preceding or following aspects, or in the alternative to some aspects, the system can be configured to be mounted on a vehicle.

In a thirty-ninth aspect, in addition to one or more of the preceding or following aspects, or in the alternative to some aspects, further can include a microfluidic channel, wherein the light source emits light into the microfluidic channel.

In a fortieth aspect, in addition to one or more of the preceding or following aspects, or in the alternative to some aspects, the system can be configured to receive information regarding a fuel level within a fuel tank and cross-reference the fuel level information against recorded information regarding detected water droplets.

In a forty-first aspect, in addition to one or more of the preceding or following aspects, or in the alternative to some aspects, the system can be configured to generate recommendations for a vehicle driver based on detected water droplets.

In a forty-second aspect, in addition to one or more of the preceding or following aspects, or in the alternative to some aspects, the recommendations include at least one of a recommended refueling location, a recommended filter type, a recommended refueling time, and a recommended vehicle service.

In a forty-third aspect, in addition to one or more of the preceding or following aspects, or in the alternative to some aspects, the system further can include a flow rate sensor.

In a forty-fourth aspect, in addition to one or more of the preceding or following aspects, or in the alternative to some aspects, the sensor controller can be configured to generate an estimate of an amount of water in a fuel based on a number of identified water droplets per unit time and a flow rate as provided by the flow rate sensor.

In a forty-fifth aspect, in addition to one or more of the preceding or following aspects, or in the alternative to some aspects, the system can be configured to identify a size distribution of water droplets based on the signals received from the light detector.

In a forty-sixth aspect, a method of monitoring water contamination in a vehicular fuel line can be included. The method can include emitting light with a light source into a microfluidic channel in fluid communication with the vehicular fuel line, receiving light from the microfluidic channel with a light detector, evaluating signals received from the light detector with a sensor controller, identifying water droplets based on a deviation in the signals received from the light detector from a baseline level, generating an estimate of an amount of water in a fuel based on the identified water droplets, and initiating generation of a notification if the estimated amount of water exceeds a threshold value.

In a forty-seventh aspect, in addition to one or more of the preceding or following aspects, or in the alternative to some aspects, the method can further include estimating a size of identified water droplets based in part on an increase and a successive decrease in the light received by the light detector with respect to a baseline level.

In a forty-eighth aspect, in addition to one or more of the preceding or following aspects, or in the alternative to some aspects, the method can further include generating the estimate of the amount of water in the fuel based on a number of identified water droplets per unit time and estimates of the size of the identified water droplets.

In a forty-ninth aspect, in addition to one or more of the preceding or following aspects, or in the alternative to some aspects, the method can further include initiating generation of a first notification if the estimated amount of water exceeds a first threshold value and a second notification if the estimated amount of water exceeds a second threshold value.

In a fiftieth aspect, in addition to one or more of the preceding or following aspects, or in the alternative to some aspects, the method can further include initiating generation of a vehicle driver notification regarding the estimated amount of water.

In a fifty-first aspect, in addition to one or more of the preceding or following aspects, or in the alternative to some aspects, the vehicle driver notification classifies the estimated amount of water as one of normal, above normal, and requiring immediate action.

In a fifty-second aspect, in addition to one or more of the preceding or following aspects, or in the alternative to some aspects, the vehicle driver notification classifies the estimated amount of water as one of normal, above normal, and requiring immediate action, as distinguished by acute and chronic water levels.

In a fifty-third aspect, in addition to one or more of the preceding or following aspects, or in the alternative to some aspects, the threshold includes a first threshold for chronic water amounts and a second threshold for acute water amounts.

In a fifty-fourth aspect, in addition to one or more of the preceding or following aspects, or in the alternative to some aspects, the method can further include identifying a size distribution of water droplets based on the signals received from the light detector.

In a fifty-fifth aspect, a water in fuel sensing system can be included having a light source, a light detector, and a sensor controller, wherein the sensor controller can be in signal communication with the light detector, wherein the sensor controller can be configured to evaluate signals received from the light detector, distinguish between air bubbles and water droplets based on the signals received from the light detector, record information regarding the water droplets, and generate an estimate of an amount of water in a fuel.

In a fifty-sixth aspect, in addition to one or more of the preceding or following aspects, or in the alternative to some aspects, the sensor controller can be configured to distinguish between air bubbles and water droplets based on at least one of peak magnitude and peak width.

In a fifty-seventh aspect, in addition to one or more of the preceding or following aspects, or in the alternative to some aspects, the sensor controller can be configured to distinguish between air bubbles and water droplets based on a ratio of peak magnitude to peak width.

In a fifty-eighth aspect, in addition to one or more of the preceding or following aspects, or in the alternative to some aspects, the sensor controller can be configured to distinguish between air bubbles and water droplets based on peak magnitude.

In a fifty-ninth aspect, in addition to one or more of the preceding or following aspects, or in the alternative to some aspects, the sensor controller can be configured to distinguish between air bubbles and water droplets based on a magnitude of a reflection peak prior to an absorbance peak.

In a sixtieth aspect, in addition to one or more of the preceding or following aspects, or in the alternative to some aspects, the water in fuel sensing system can be an on-vehicle sensing system.

In a sixty-first aspect, in addition to one or more of the preceding or following aspects, or in the alternative to some aspects, further can include a sampling channel, wherein the sampling channel can be in fluid communication with a fuel line of a vehicle.

In a sixty-second aspect, in addition to one or more of the preceding or following aspects, or in the alternative to some aspects, the light source can be configured to emit light into the sampling channel.

In a sixty-third aspect, in addition to one or more of the preceding or following aspects, or in the alternative to some aspects, the water in fuel sensing system can be configured to generate the estimate of the amount of water in the fuel based on an estimated size of water droplets and an estimated number of water droplets.

In a sixty-fourth aspect, in addition to one or more of the preceding or following aspects, or in the alternative to some aspects, the light source can be configured to emit near-infrared light.

In a sixty-fifth aspect, a water in fuel sensing system can be included having a light source, a first light detector, a second light detector, and a sensor controller, wherein the sensor controller can be in signal communication with the first light detector and the second light detector and wherein the sensor controller can be configured to evaluate signals received from the first light detector and the second light detector, distinguish between air bubbles and water droplets based on the signals received from the first light detector and the second light detector, record information regarding the water droplets, and generate an estimate of an amount of water in a fuel.

In a sixty-sixth aspect, in addition to one or more of the preceding or following aspects, or in the alternative to some aspects, wherein the first light detector can be positioned to detect absorbance of light by a fluid passing through the water in fuel sensing system, and wherein the second light detector can be positioned to detect reflection of light from bubbles within the fluid passing through the water in fuel sensing system.

In a sixty-seventh aspect, in addition to one or more of the preceding or following aspects, or in the alternative to some aspects, the sensor controller can be configured to distinguish between air bubbles and water droplets based on a magnitude of a reflection peak prior to an absorbance peak.

In a sixty-eighth aspect, in addition to one or more of the preceding or following aspects, or in the alternative to some aspects, the sensor controller can be configured to distinguish between air bubbles and water droplets based on peak magnitude.

In a sixty-ninth aspect, in addition to one or more of the preceding or following aspects, or in the alternative to some aspects, the water in fuel sensing system can be an on-vehicle sensing system.

In a seventieth aspect, in addition to one or more of the preceding or following aspects, or in the alternative to some aspects, further can include a sampling channel, wherein the sampling channel can be in fluid communication with a fuel line of a vehicle.

In a seventy-first aspect, in addition to one or more of the preceding or following aspects, or in the alternative to some aspects, the light source can be configured to emit light into the sampling channel.

In a seventy-second aspect, in addition to one or more of the preceding or following aspects, or in the alternative to some aspects, the water in fuel sensing system can be configured to generate the estimate of the amount of water in the fuel based on an estimated size of water droplets and an estimated number of water droplets.

In a seventy-third aspect, in addition to one or more of the preceding or following aspects, or in the alternative to some aspects, the light source can be configured to emit near-infrared light.

In a seventy-fourth aspect, a water in fuel sensing system can be included having a first light source, wherein the first light source can be configured to emit near-infrared light, a second light source, wherein the second light source can be configured to emit light within the visible spectrum, a first light detector, wherein the first light detector can be configured to detect light emitted from the first light source after it can have passed through a fuel, a second light detector, wherein the second light detector can be configured to detect light emitted from the second light source after it can have passed through the fuel, and a sensor controller. The sensor controller can be in signal communication with the first light detector and the second light detector and can be configured to evaluate signals received from the first light detector and the second light detector, distinguish between air bubbles and water droplets based on the signals received from the first light detector and the second light detector, record information regarding the water droplets, and generate an estimate of an amount of water in a fuel.

In a seventy-fifth aspect, in addition to one or more of the preceding or following aspects, or in the alternative to some aspects, the sensor controller can be configured to distinguish between air bubbles and water droplets based on a magnitude of peaks detected by the first light detector relative to a magnitude of peaks detected by the second light detector.

In a seventy-sixth aspect, in addition to one or more of the preceding or following aspects, or in the alternative to some aspects, the water in fuel sensing system can be an on-vehicle sensing system.

In a seventy-seventh aspect, in addition to one or more of the preceding or following aspects, or in the alternative to some aspects, further can include a sampling channel, wherein the sampling channel can be in fluid communication with a fuel line of a vehicle.

In a seventy-eighth aspect, in addition to one or more of the preceding or following aspects, or in the alternative to some aspects, the first light source and the second light source can be configured to emit light into the sampling channel.

In a seventy-ninth aspect, in addition to one or more of the preceding or following aspects, or in the alternative to some aspects, the water in fuel sensing system can be configured to generate the estimate of the amount of water in the fuel based on an estimated size of water droplets and an estimated number of water droplets.

In an eightieth aspect, a water in fuel sensing system can be included having a light source, a light detector, and a sampling channel, wherein the light source can be configured to emit light into the sampling channel, wherein the sampling channel can be in fluid communication with a fuel line of a vehicle, a sensor controller. The sensor controller can be in signal communication with the light detector and can be configured to evaluate signals received from the light detector, wherein the sensor controller can be configured to identify water droplets based on the signals received from the light detector, wherein the sensor controller can be configured to record information regarding the water droplets, and wherein the sensor controller can be configured to generate an estimate of an amount of water in a fuel.

In an eighty-first aspect, in addition to one or more of the preceding or following aspects, or in the alternative to some aspects, the water in fuel sensing system can be an on-vehicle sensing system.

In an eighty-second aspect, in addition to one or more of the preceding or following aspects, or in the alternative to some aspects, the water in fuel sensing system can be configured to generate the estimate of the amount of water in the fuel based on an estimated size of water droplets and an estimated number of water droplets.

In an eighty-third aspect, in addition to one or more of the preceding or following aspects, or in the alternative to some aspects, the light source can be configured to emit near-infrared light.

In an eighty-fourth aspect, in addition to one or more of the preceding or following aspects, or in the alternative to some aspects, an inlet to the sampling channel can be located along a curved portion of a fuel flow channel.

In an eighty-fifth aspect, in addition to one or more of the preceding or following aspects, or in the alternative to some aspects, further can include a shield disposed within the fuel line configured to prevent air bubbles from entering an inlet to the sampling channel.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
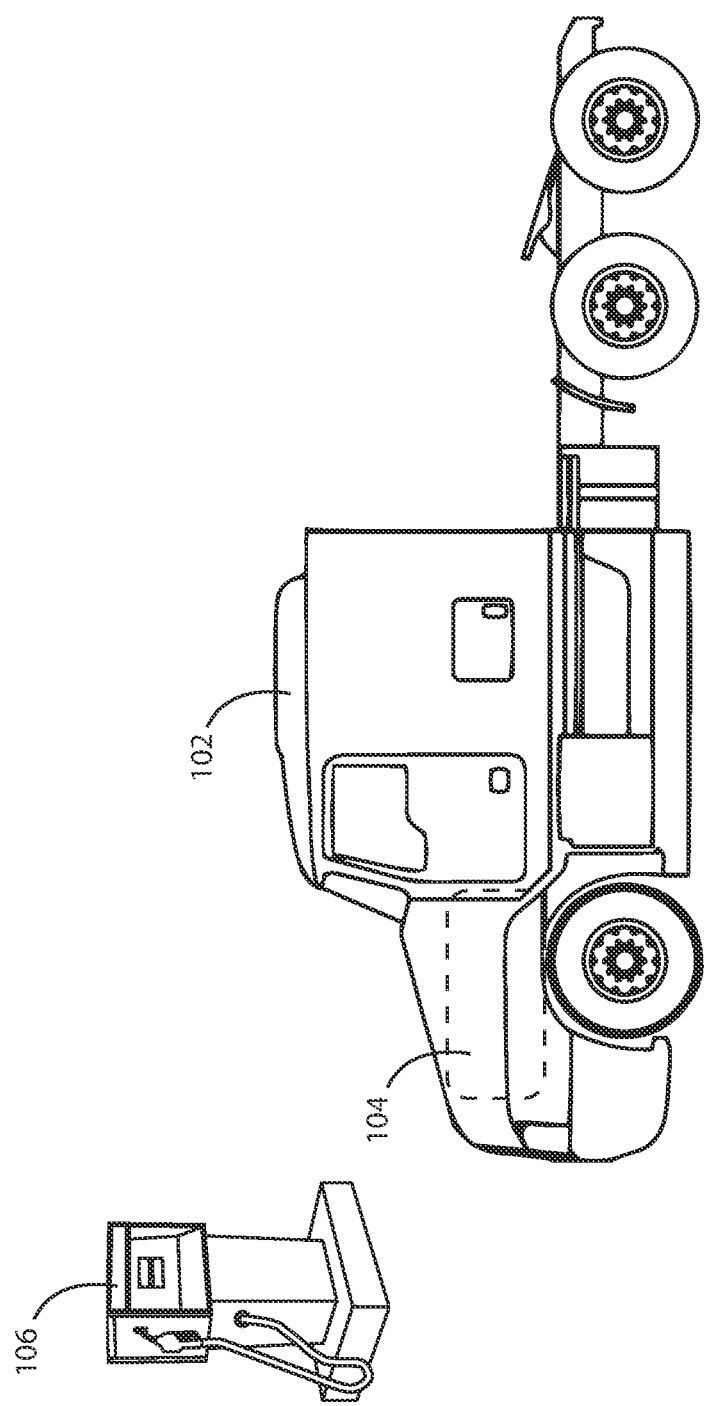
FIG. 1 is a schematic view of a vehicle with a water in fuel sensing system in accordance with various embodiments herein.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As discussed above, one contaminant in fuel is water. Water in fuel causes corrosion and will erode injector nozzles. It can negatively affect the combustion process, reduce the lubricity of the fuel and consequently damage system components. Water enters fuel from, amongst other things, storage tanks and from condensation caused by cooling temperatures.

Embodiments herein include on-vehicle water in fuel sensing systems that can detect the presence of water contamination along with providing estimates of the amount of water contamination. By being on-vehicle, the system can provide information that may be useful to a vehicle operator, fleet controller, or the like to help determine the possible cause of fuel contamination (e.g., filled up at a fueling station that had water contamination) as well as provide information to support operation of the vehicle while mitigating damage. For example, in some scenarios, if the level of water in fuel rose above a threshold level, then a recommendation to discontinue operation of the vehicle could be made. As another example, the level of water in fuel for a vehicle can result in recommendations being made by the system related to servicing of the vehicle including servicing frequency, the type of fuel filter being used, and the like. The system can evaluate both short term (or acute) water level information along with long term (or chronic) water level information in order to provide complete information that is actionable by a vehicle operator, fleet controller, or the like.

In various embodiments, a water in fuel sensing system herein can include a light source, a light detector, and a sensor controller. The sensor controller can be in signal communication with the light detector. The sensor controller can be configured to evaluate signals received from the light detector, identify water droplets based on the signals received from the light detector, record information regarding the classified water droplets, and generate an estimate of the amount of water in a fuel.

In various embodiments herein, a water contamination monitoring system for a vehicle is included that can have a light source, a light detector, and a sensor controller. The sensor controller can be in electronic communication with the light detector and can be configured to evaluate signals received from the light detector, detect water droplets based a deviation from a baseline value, estimate water droplet size based on evaluating both any rise in the signals received from the light detector and any fall in the signals received from the light detector below the baseline value, and record and/or transmit information regarding the detected water droplets.

In various embodiments herein, a water in fuel sensing system can distinguish between air bubbles and water droplets to allow for more accurate measurements of amounts of water in fuel. In various embodiments, the sensor controller can be configured to evaluate signals received from the light detector, distinguish between air bubbles and water droplets based on the signals received from the light detector, record information regarding the water droplets; and generate an estimate of an amount of water in a fuel.

Referring now to FIG. 1, a schematic view of a vehicle 102 with a water in fuel sensing system is shown in accordance with various embodiments herein. The vehicle 102 includes a fuel system 104. FIG. 1 shows a fueling station 106. The vehicle 102 can obtain fuel from the fueling station 106. However, a water in fuel sensing system (not shown in this view) can be configured to be mounted on a vehicle 102. As such, if there is water contamination of the fuel from the fueling station 106, the system can detect this and provide information to a vehicle operator, fleet controller, or the like. In some cases, such as in the case of a vehicle fleet, the information can be sent to the fleet controller or similar central control system in order to prevent other vehicles in the fleet from fueling at the same fueling station 106. In some embodiments, a notification can be sent to an operation of the fueling station 106 to alert them to the water contamination issue.

Figure 2:
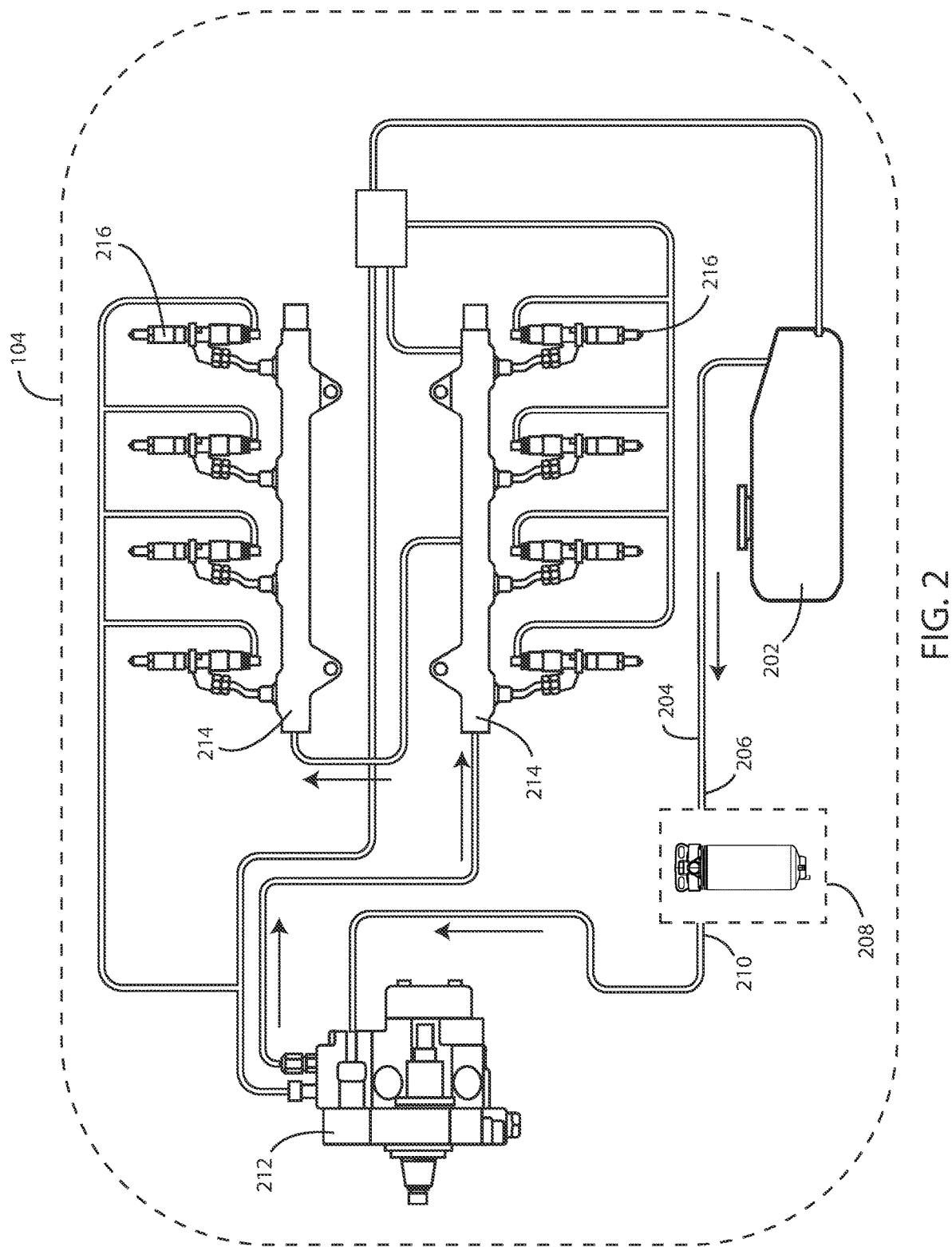
FIG. 2 is a schematic view of a fuel system in accordance with various embodiments herein.

Referring now to FIG. 2, a schematic view of a fuel system 104 is shown in accordance with various embodiments herein. The fuel system 104 can include various components such as a fuel tank 202, a fuel line 204, and a fuel filter system 208. The fuel system 104 can also include a fuel pump 212, a fuel rail 214, and a plurality of fuel injectors 216. The fuel line 204 includes an upstream side 206 (e.g., upstream from the fuel filter system 208) and a downstream 210 side.

A water in fuel sensing system herein can be mounted at various points along the fuel system 104. In some embodiments, the water in fuel sensing system (or components thereof) can be mounted along a fuel line 204. In various embodiments, the water in fuel sensing system can be mounted upstream 206 from a fuel filter. In various embodiments, the water in fuel sensing system can be mounted downstream 210 from a fuel filter. In various embodiments, the water in fuel sensing system can be mounted on or in a fuel filter head (described further below).

In some embodiments, the system can be configured to receive information regarding a fuel level within the fuel tank 202. For example, in some embodiments, the system can cross-reference the fuel level information against recorded information regarding detected water droplets. In some cases, the system can get the fuel level data directly from a sensor that is associated with the fuel tank. In some embodiments, the system can get the fuel level data from a vehicle data network, such as CANBus. "CANBus" refers to a vehicle data bus standard designed to allow devices and electronic control units to communicate with one another. Many vehicles include a CANBus network and communication with the CANBus network can provide many different types of data. For example, interfacing with the CANBus network can provide one or more of fuel level data, engine RPM data, engine hours of operation data, odometer data, engine/vehicle temperature data, fuel consumption data, fuel system data, ambient temperature data, geolocation data, fuel flowrate and the like.

Figure 3:
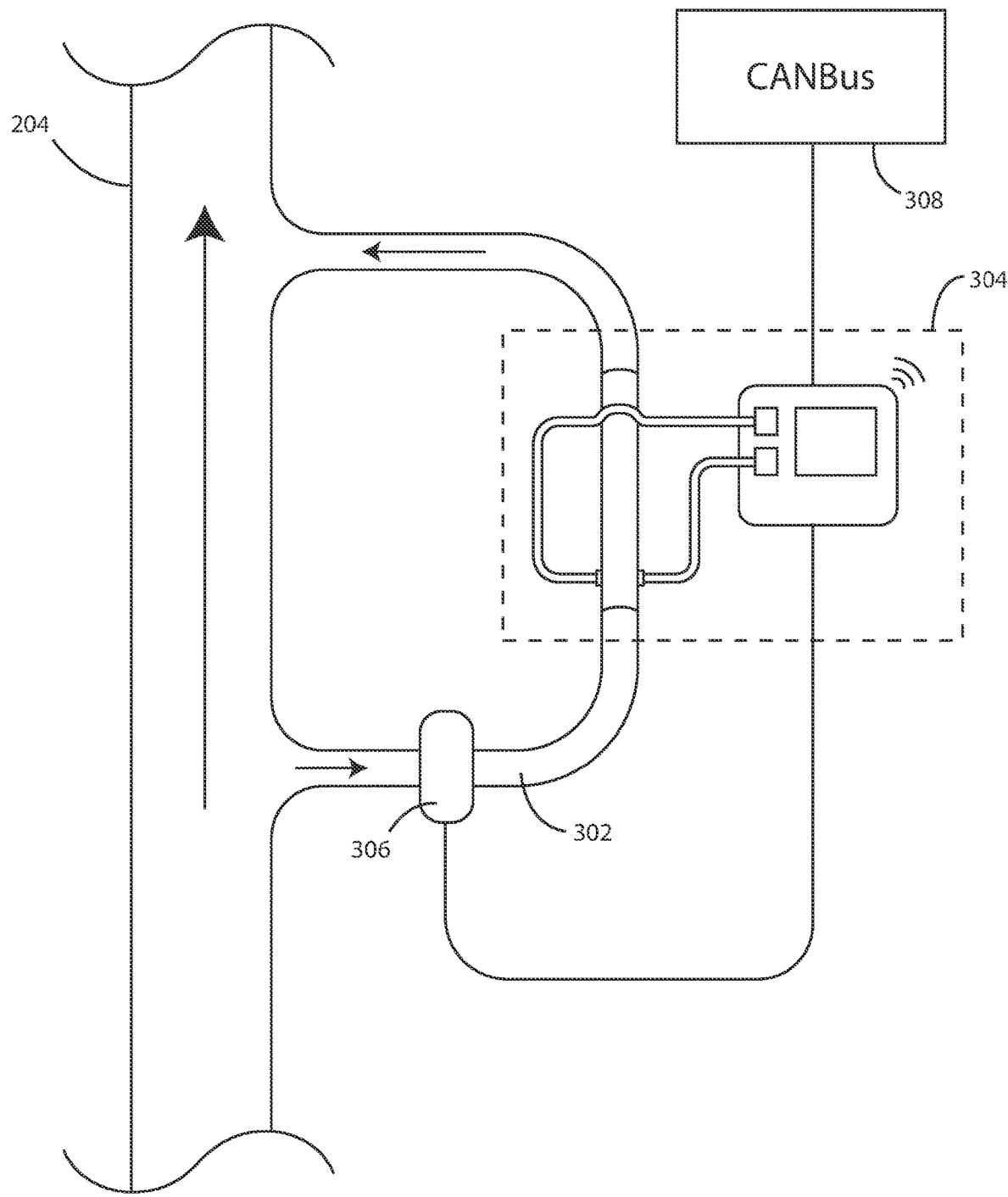
FIG. 3 is a schematic view of a water sensing system in accordance with various embodiments herein.

Referring now to FIG. 3, a schematic view of a water in fuel sensing system 304 is shown in accordance with various embodiments herein. As noted before, the water in fuel sensing system 304 can be configured to be mounted on a vehicle. FIG. 3 shows the fuel line 204 of the vehicle. FIG. 3 shows a water in fuel sensing system 304. The water in fuel sensing system 304 includes a flow channel 302. The flow channel 302 can be in fluid communication with the fuel line 204 of a vehicle 102. Thus, a portion of the fuel that is flowing through the fuel line 204 can enter the flow channel 302 for testing by the water in fuel sensing system 304.

In various embodiments herein, data regarding a flow rate can be used in combination with data regarding the number of water droplets detected and the size of the water droplets detected in order to estimate the total amount of water in the fuel. It will be appreciated that there are at least two potentially different fuel flow rates to consider in making such a calculation. The first is the engine fuel flow rate. The second is the sensor fuel flow rate, which is the flow rate of fuel through the flow channel 302 of the water in fuel sensing system 304 described in FIG. 3. The engine fuel flow rate can vary based on various factors including the operating state and/or load of the engine, but will typically be on the order of liters per minute. For example, typical ranges for a given engine could be from 1 to 4 liters per minute (lpm) or from 2 to 10 lpm. The engine flow rate could go up to 17 lpm or higher in some applications. The sensor flowrate is much lower, but varies along with the engine fuel flow rate. The sensor flow rate could be from 0.2 mlpm (milliliters per minute) to 2 mlpm or from 0.8 mlpm to 1.2 mlpm. The sensor flowrate is related to the engine flow rate so as the engine flow rate changes the sensor flow rate will also change. Converting from one flow rate to the other can be a matter of applying a simple calibration or relationship equation. In some embodiments, the system can store data in a lookup table or similar data structure that relates the sensor flow rate and the engine flow rate at various values for each and then converting between the two can simply be a matter of referencing the lookup table. In some embodiments, data relating the sensor flow rate and the engine flow rate can be determined empirically.

In some embodiments, the water in fuel sensing system 304 also includes a flow rate sensor 306. Data from the flow rate sensor 306 can be used, in combination with data regarding the number of water droplets detected and the size of the water droplets detected in order to estimate the total amount of water in the fuel. In some embodiments, the flow rate sensor 306 can be positioned so that it is detecting the sensor fuel flow rate. In calculating/estimating the total amount of water in the fuel, the sensor fuel flow rate can be determined and then this information can be used in combination with data regarding the number of water droplets detected and the size of the water droplets detected in order to estimate the total amount of water in the fuel. However, in some cases, a flow rate sensor may be positioned along a fuel line of the engine such that the flow rate obtained is the engine fuel flow rate. In such cases, the engine fuel flow rate can be converted to a sensor flow rate as discussed above.

In some embodiments, data regarding fuel flow rates can be obtained in other ways and thus a flow rate sensor 306 may be omitted. For example, in some embodiments differential pressure (dP) can be used to calculate/estimate flow rate. The flow rate estimated in this manner can be either the engine fuel flow rate or the sensor fuel flow rate. The system can include a differential pressure sensor and then calculate flow rate based on the relationship between dP and flow rate along using an assumption of laminar flow and knowledge of fluid fuel properties. As another example, in some embodiments, the water in fuel sensing system 304 can get information regarding fuel flow rates (or a piece of information from which fuel flow rates can be derived or otherwise estimated) from a vehicular data network 308. In some embodiments, the vehicular data network 308 can be a CANBUS network. But, in other embodiments the vehicular data network 308 can be another type of network that is wired or wireless. In various embodiments, the water in fuel sensing system 304 can be configured to send information regarding the identified water droplets to a vehicular data network 308.

Figure 4:
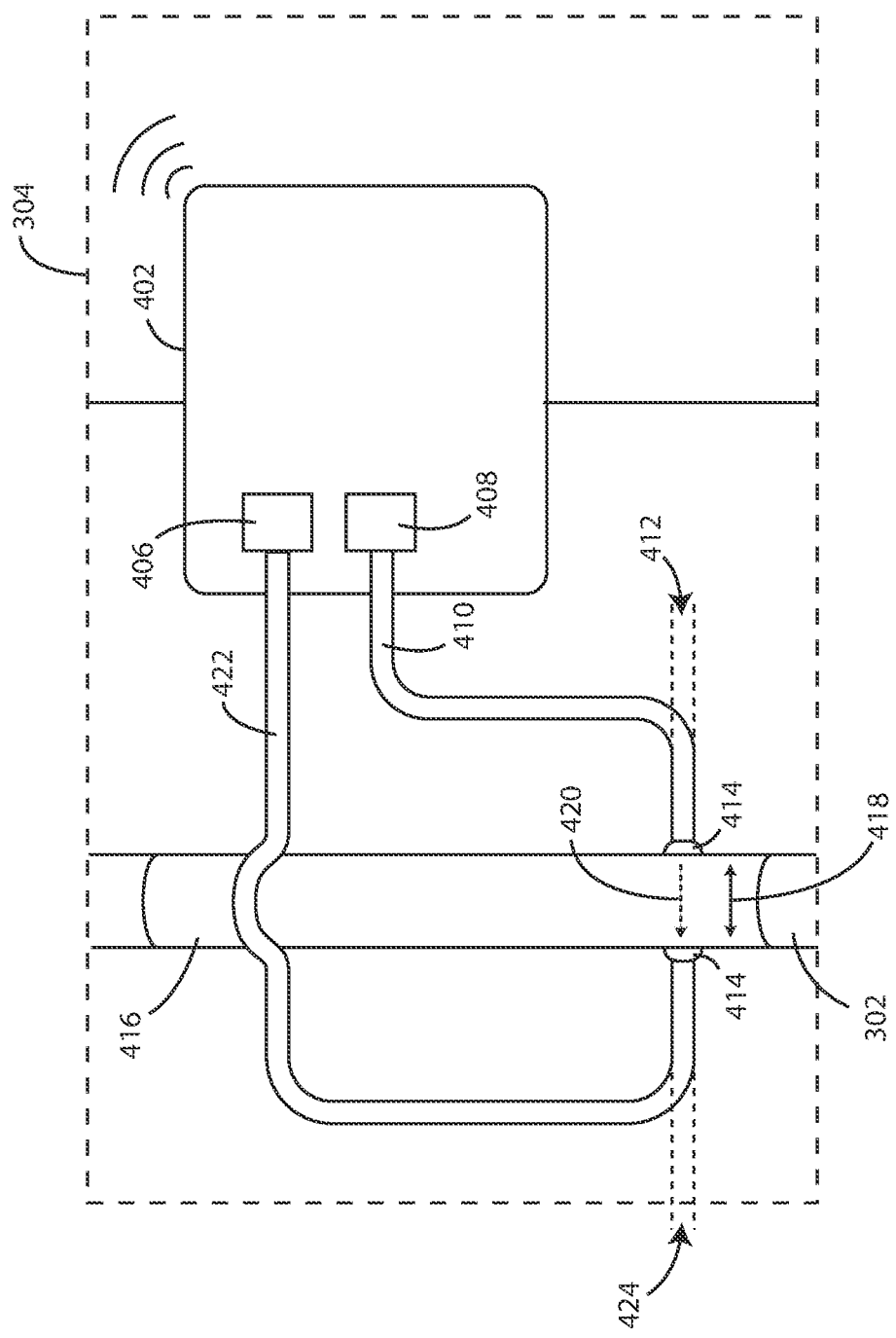
FIG. 4 is a schematic view of a water sensing system in accordance with various embodiments herein.

Referring now to FIG. 4, a schematic view of components of a water in fuel sensing system is shown in accordance with various embodiments herein. FIG. 4 shows a water in fuel sensing system 304 including a flow channel 302. Fuel can flow from the fuel line (or a component connected to the fuel line) of the vehicle and into the flow channel. In some embodiments, the water in fuel sensing system 304 also includes a flow cell 416. The flow cell 416 can be transparent, partially transparent, or at least include transparent portions and can be formed of various materials such as a glass or a polymer. The flow cell 416 (or another vessel with provisional for optical transmission) can be connected to the flow channel 302. Thus, fuel can pass through the flow channel 302.

The water in fuel sensing system 304 includes a light source 408. The water in fuel sensing system 304 also includes a source light guide 410. In some embodiments, the water in fuel sensing system 304 also includes an optical interface 414 providing an optical connection between the source light guide 410 and the flow cell 416. In this manner, a light emission 420 generated by the light source 408 can pass through the fuel in the flow cell 416.

A second optical interface 414 can provide an optical connection between the flow cell 416 and a detector light guide 422. The water in fuel sensing system 304 also includes a light detector 406 that in optical communication with the detector light guide 422. In some embodiments, the light source 408, the light detector 406, and various other components can be disposed within a housing 402.

In some embodiments, the light source 408 can be a LED or other light emitter. In some embodiment, the light detector 406 can be a photodiode, phototransistor, photoresistor, CMOS sensor, a charge-coupled device, or the like. The source light guide 410 can be an optical fiber, a light pipe, or other structure capable of conveying an optical signal. Similarly, the detector light guide 422 can be an optical fiber, a light pipe, other structure capable of conveying an optical signal.

In operation, the light source can be configured to emit light into a sample of fuel (directly or indirectly) and the light detector can be configured to receive light that has passed through the sample (directly or indirectly). In the example of FIG. 4, the light source and light detector can be arranged to be in optical communication with components on opposing sides of the flow cell 416. The absorbance of water at certain wavelengths of light (including, but not limited to, near infrared light or light centered at a wavelength of about 1550 nanometers) is different than that of fuel. Therefore, a signal from the light detector will vary based upon the amount of water in the fuel. The signal from the light detector can then be evaluated to determine the amount of water in the fuel passing through the sensor channel.

The flow channel 302 includes a channel diameter 418. The channel diameter 418 can have a diameter of various dimensions. In some embodiments, the diameter can be greater than or equal to 100 μm, 130 μm, 160 μm, 190 μm, 220 μm, or 250 μm. In some embodiments, the diameter can be less than or equal to 1000 μm, 850 μm, 700 μm, 550 μm, 400 μm, or 250 μm. In some embodiments, the diameter can fall within a range of 100 μm to 1000 μm, or 130 μm to 850 μm, or 160 μm to 700 μm, or 190 μm to 550 μm, or 220 μm to 400 μm.

The source light guide 410 can have a particular diameter 412. In some embodiments, the diameter 412 can be greater than or equal to 100 μm, 200 μm, 250 μm, 300 μm, 350 μm, or 400 μm. In some embodiments, the diameter 412 can be less than or equal to 800 μm, 700 μm, 600 μm, 500 μm, or 400 μm. In some embodiments, the diameter 412 can fall within a range of 100 μm to 800 μm, or 150 μm to 500 μm, or 200 μm to 300 μm, or 250 μm to 350 μm, or can be about 300 μm.

The detector light guide 422 can have a particular diameter 424. In some embodiments, the diameter 424 of the detector light guide 422 is less than the diameter 412 of the source light guide 410. In some embodiments, the diameter 424 can be greater than or equal to 100 μm, 125 μm, 150 μm, 175 μm, or 200 μm. In some embodiments, the diameter 424 can be less than or equal to 400 μm, 350 μm, 300 μm, 250 μm, or 200 μm. In some embodiments, the diameter 424 can fall within a range of 100 μm to 400 μm, or 125 μm to 350 μm, or 150 μm to 300 μm, or 175 μm to 250 μm, or can be about 200 μm.

Figure 5:
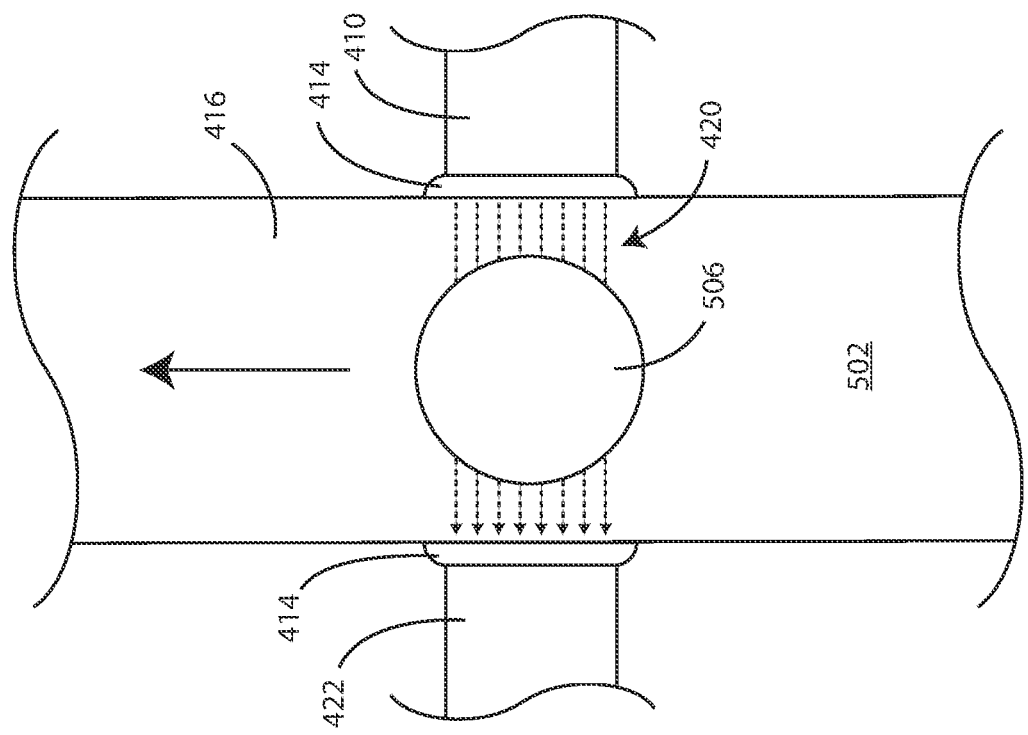
FIG. 5 is a schematic view of a portion of a water sensing system in accordance with various embodiments herein.

Referring now to FIG. 5, a schematic view of a portion of a water sensing system is shown in accordance with various embodiments herein. Fuel moves through a flow path 502 defined by the flow cell 416. A light emission 420 from a light source (not shown in this view) passes from the source light guide 410 to the optical interface 414, and then across the flow path 502 wherein it can encounter a water droplet 506. The light emission (as altered by its interactions with the water droplet 506) then passes through the other optical interface 414 before entering the detector light guide 422.

Figure 6:
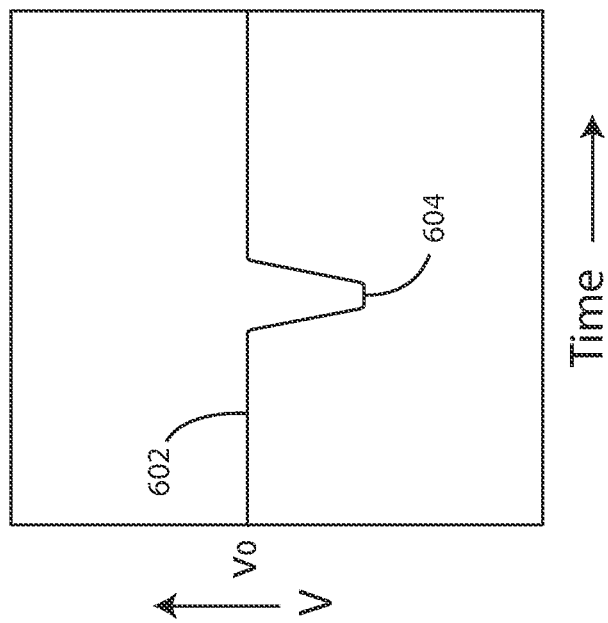
FIG. 6 is a view of potential versus time for a sensing system in accordance with various embodiments herein.

The light passing through the detector light guide 422 can then pass to the light detector (not shown in this view) which can generate a signal based on the received light. Referring now to FIG. 6, a view of electrical potential versus time is shown for a sensing system in accordance with various embodiments herein. The varying electrical potential serves as one example of a signal that can be generated based on the light received by the light detector. In this example, a baseline 602 is shown which is indicative of just fuel in the flow path. However, FIG. 6 also shows a negative deviation 604. This can be indicative of a droplet of water in the flow path that is absorbing some amount of the light or otherwise preventing some amount of the light from entering the detector light guide 422. Thus, in various embodiments, the system and/or a sensor controller thereof can be configured to identify water droplets based on a deviation in the signals received from the light detector from the baseline 602 level.

Remarkably, it has been found herein that large water droplets actually generate an upward deviation in the signal over a baseline level before later falling below the baseline level (e.g., a sequence of a positive deviation from baseline following by a negative deviation from the baseline). As such, the size of droplets can be detected by evaluating the signals received and specifically determining if there was only a negative deviation or if there was an initial positive deviation followed by a negative deviation.

Figure 7:
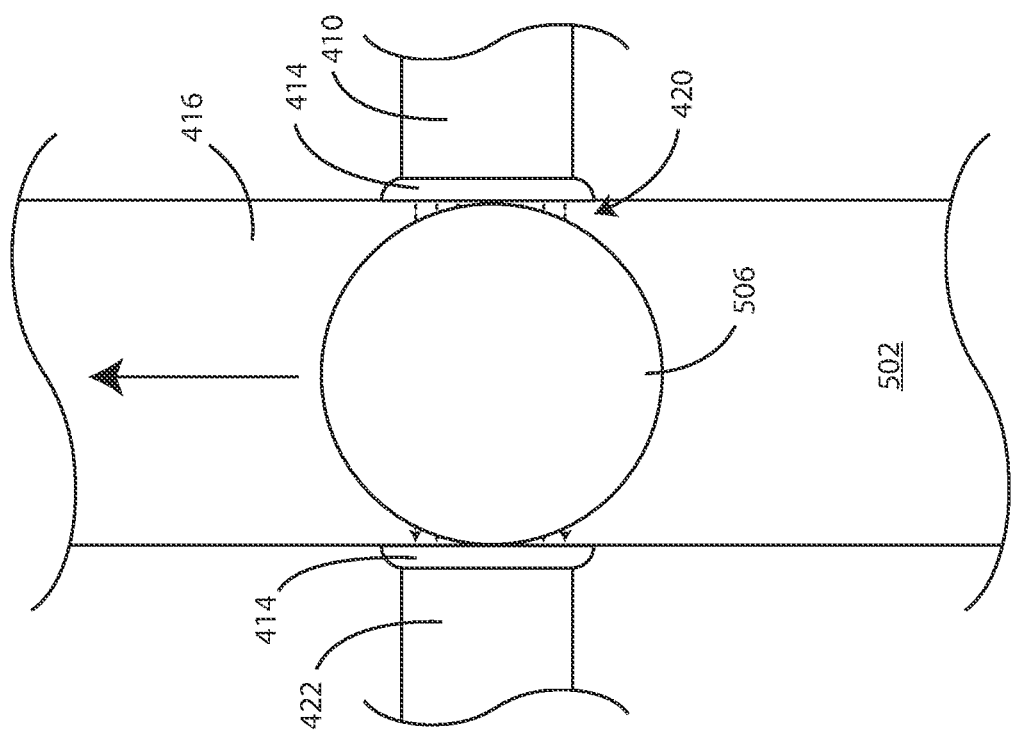
FIG. 7 is a schematic view of a portion of a water sensing system in accordance with various embodiments herein.

Referring now to FIG. 7, a schematic view of a portion of a water sensing system is shown in accordance with various embodiments herein. As before, fuel moves through a flow path 502 defined by the flow cell 416. A light emission 420 from a light source (not shown in this view) passes from the source light guide 410 to the optical interface 414, and then across the flow path 502 wherein it can encounter a water droplet 506. The light emission (as altered by its interactions with the water droplet 506) then passes through the other optical interface 414 before entering the detector light guide 422.

Figure 8:
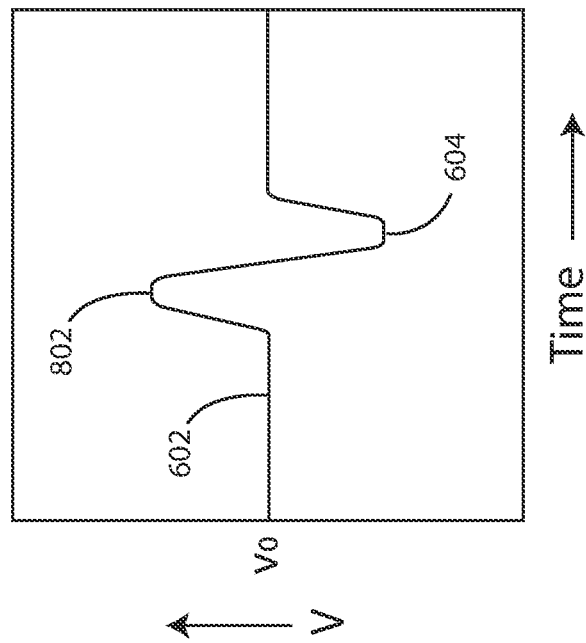
FIG. 8 is a view of potential versus time for a sensing system in accordance with various embodiments herein.

However, this time the negative deviation in the signal is preceded by a positive deviation in the signal. Referring now to FIG. 8, a view of potential versus time for a sensing system is shown in accordance with various embodiments herein. FIG. 8 shows a baseline 602 value that is maintained initially and then a positive deviation 802 followed by a negative deviation 604. This pattern is indicative of a relatively large water droplet as compared with a water droplet that only caused a negative deviation.

Further size information about the water droplets can also be gathered. For example, an extremely large water droplet can cause a negative deviation (after an initial positive deviation) that holds the sensor signal at the negative value for a period of time that is longer than a smaller droplet.

Figure 9:
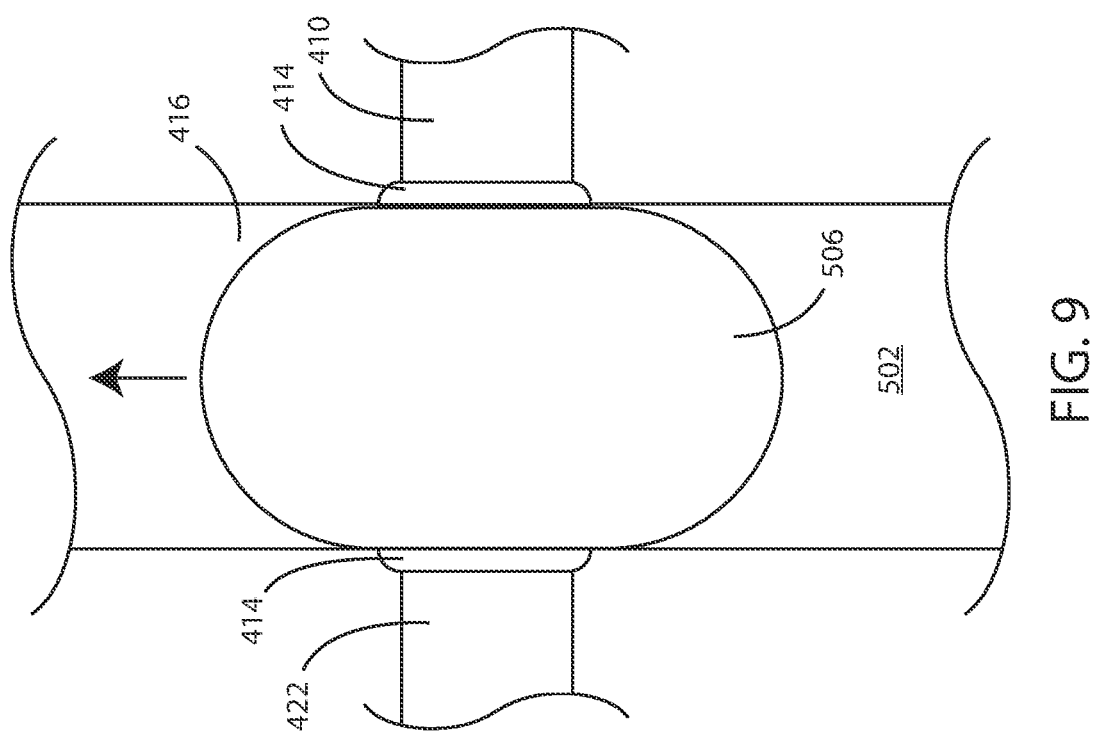
FIG. 9 is a schematic view of a portion of a water sensing system in accordance with various embodiments herein.

Referring now to FIG. 9, a schematic view of a portion of a water sensing system is shown in accordance with various embodiments herein. As before, fuel moves through a flow path 502 defined by the flow cell 416. A light emission 420 from a light source (not shown in this view) passes from the source light guide 410 to the optical interface 414, and then across the flow path 502 wherein it can encounter a water droplet 506. The light emission (as altered by its interactions with the water droplet 506) then passes through the other optical interface 414 before entering the detector light guide 422.

Figure 10:
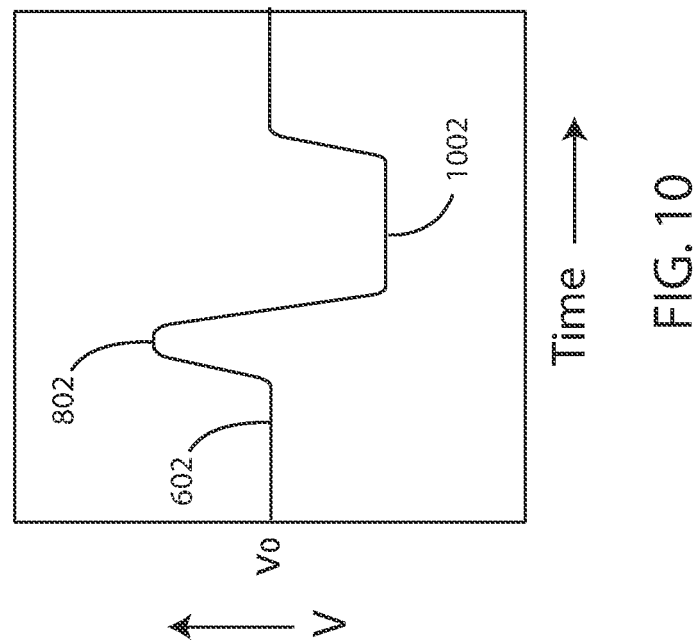
FIG. 10 is a view of potential versus time for a sensing system in accordance with various embodiments herein.

FIG. 10 shows a view of electrical potential versus time for the sensing system is shown in accordance with various embodiments herein. FIG. 10 shows a baseline 602 being maintained initially followed by a positive deviation 802 and an extended negative deviation 1002.

Figure 11:
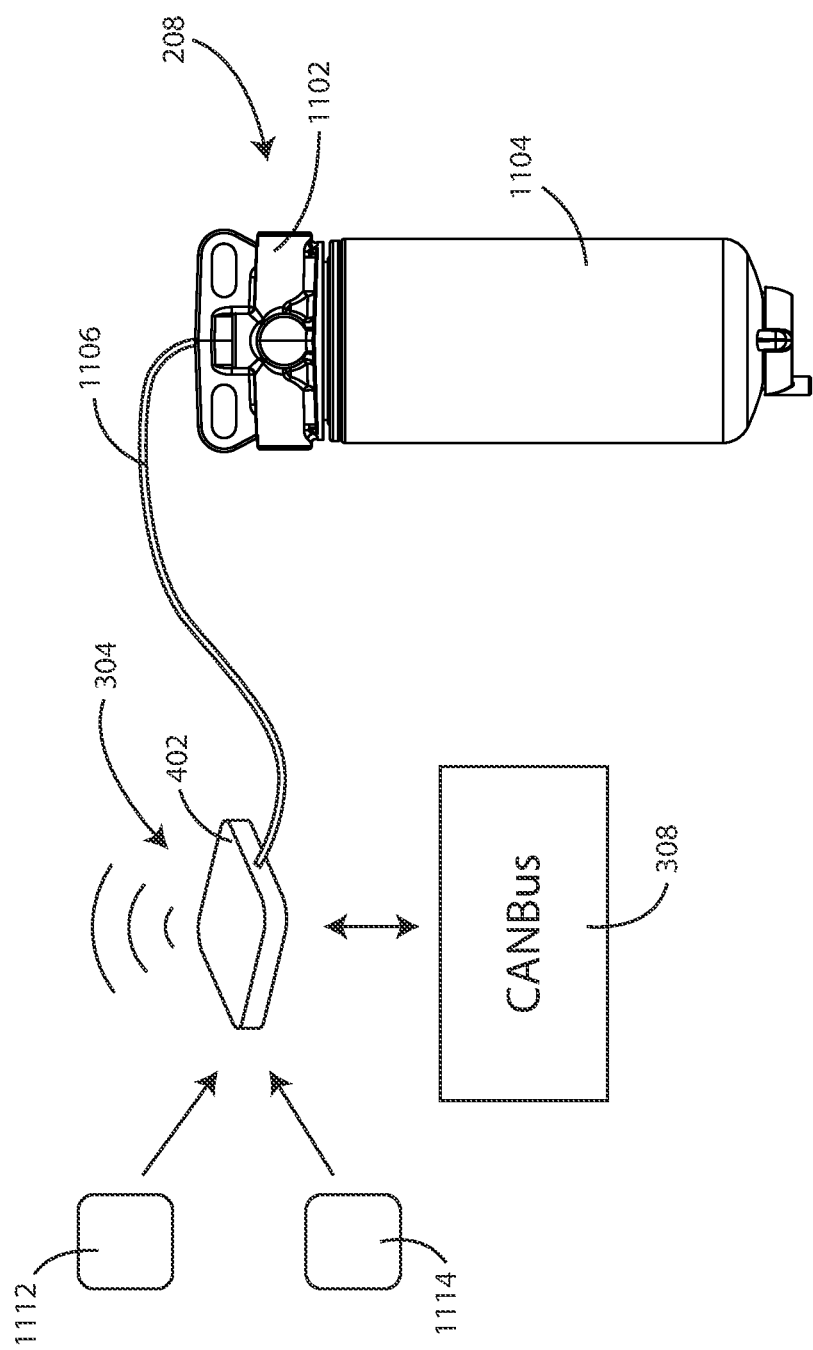
FIG. 11 is a schematic view of a water sensing system in accordance with various embodiments herein.

Referring now to FIG. 11, a schematic view of components of a system herein are shown in accordance with various embodiments herein. The system can include a fuel filter system 208. The fuel filter system 208 can include a filter head 1102 and a filter unit 1104.

FIG. 11 also shows a housing 402 of a water in fuel sensing system 304. The housing 402 can be connected to the fuel filter system 208 via control cable 1106, which can include electrical wires and/or optical fibers therein. While FIG. 11 depicts the housing 402 separately from the fuel filter system 208, it will be appreciated that in various embodiments herein, the housing 402 or other components of the water in fuel sensing system 304 can be physically integrated into the fuel filter system 208 and/or mounted thereon. Further, in some embodiments, the water in fuel sensing system 304 does not interface with the fuel filter system 208, but rather interfaces with the fuel line or a component connected to the fuel line at a different point of the fuel system.

The water in fuel sensing system 304 can include one or more components or sensor devices and/or can be configured to receive data from one or more components or sensor devices. By way of example, the water in fuel sensing system 304 can interface with vehicular data network 308. In some embodiments, the vehicular data network 308 can be a CANBus network. However, the vehicular data network 308 can also be (or connect to) other types of data networks. Interface with a vehicular data network can be via wired or wireless protocols.

In some embodiments, water in fuel sensing system 304 can be in communication with a first additional data generating or receiving device 1112 and/or a second additional data generating or receiving device 1114. Data can include, but are not limited to, one or more of geolocation data, weather data, temperature data, pressure data, humidity data, fuel filter model number, engine model number, driver ID, and detected refueling times.

In some the water in fuel sensing system 304 can also include other types of contaminant sensors. For example, the first or second additional data generating and/or receiving device can include or can be in communication with another type of fuel contaminant sensor. In various embodiments herein, the system can then correlate refueling locations with subsequent changes in the contaminant levels as identified (at least partially) by a contaminant sensor to identify an effect of specific refueling locations on contaminant levels and therefore on the amount of contaminants in the fuel. Such contaminant sensors can include, but are not limited to, on-vehicle particulate counters/monitors. In some embodiments, the contaminant sensor can include an optical-based sensor that uses detection of light blocking for particle detection. For example, particles can pass through an optical flow cell including a lighter emitter. The particles can block portions of the light, creating a shadow. These shadows can be detected by a light detector. Contaminant sensors can also rely upon other methods of detection other than light based optical systems. For example, contaminant sensors can also rely upon electrical, magnetic, weight, and/or density properties in order to detect contaminants. In some embodiments, a contaminant sensor herein can detect particles in accordance with ISO 11171 regarding particle count data in fluids. It will be appreciated that data from other types of contaminant sensors (and specifically data from particulate counters/monitors) can be used in isolation or in combination with other types of contaminant data or restriction data discussed herein.

Figure 12:
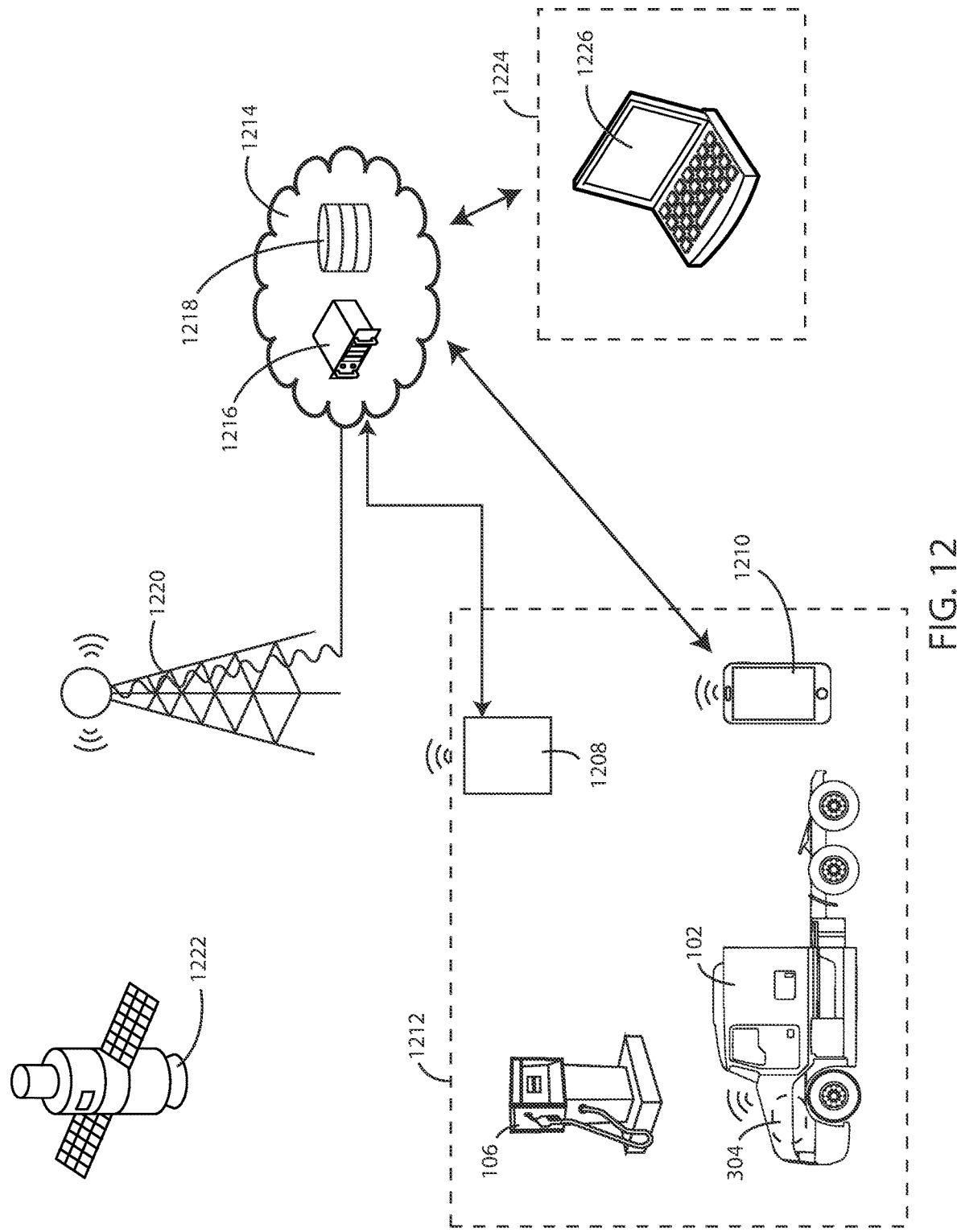
FIG. 12 is a schematic view of a water sensing system in accordance with various embodiments herein.

Referring now to FIG. 12, a schematic view of a system is shown in accordance with various embodiments herein. FIG. 12 shows a vehicle 102. The vehicle 102 includes a fuel system 104 including a water in fuel sensing system. In FIG. 12, the vehicle 102 is shown at a refueling location 1212. The refueling location 1212 includes a fueling station 106.

In some cases, the water in fuel sensing system 304 can be capable of direct wireless data communication to the cloud 122 or to another data network. In some cases, the water in fuel sensing system 304 can be capable of indirect wireless data communication to the cloud 122 or to another data network. In some embodiments, the water in fuel sensing system 304 can communicate with a cell tower 1220, which in turn can relay data communications back and forth with the cloud 1214 and components thereof such as servers 1216 (real or virtual) and databases 1218 (real or virtual).

Wireless communication can take place using various protocols. For example, wireless communications/signals exchanged between the fuel filter system 208 and/or the water in fuel sensing system and the cloud 1214 (or between components of the fuel filter system 208 and/or the water in fuel sensing system) can follow many different communication protocol standards and can be conducted through radiofrequency transmissions, inductively, magnetically, optically, or even through a wired connection in some embodiments. In some embodiments herein, IEEE 802.11 (e.g., WIFI®), BLUETOOTH® (e.g., BLE, BLUETOOTH® 4.2 or 5.0), ZIGBEE®, or a cellular transmission protocol/platform can be used such as CDMA, cdmaOne, CDMA2000, TDMA, GSM, IS-95, LTE, 5G, GPRS, EV-DO, EDGE, UMTS, HSDPA, HSUPA, HSPA+, TD-SCDMA, WiMAX, and the like. In various embodiments, a different standard or proprietary wireless communication protocol can also be used.

As referenced, cloud 1214 resources may include databases 1218. Such databases 1218 can store various pieces of information including, but not limited to, refueling location data (such as refueling location IDs, refueling location geolocation data, fuel filter loading rate data related to specific refueling locations, refueling location estimated impurity/contamination information, refueling location visit data, refueling location filter loading impact data, and the like), fleet data, vehicle data, filtration system data, and the like.

It will be appreciated that database content may be spread across many different physical systems, devices, and locations. Further, while not depicted in FIG. 12, it will be appreciated that database records can also be stored at the level of the water in fuel sensing system 304. In various embodiments, the database 1218 or portions thereof can be stored at a location remote from other components of the system, such as the water in fuel sensing system 304. In some embodiments, records or portions of the database can be stored across different physical locations and, in some embodiments, cached across different physical locations for ready access.

In some embodiments, the refueling location 1212 can include a location communication device 1208. The location communication device 1208 can include various components. In some embodiments, the location communication device 1208 can be a wireless data gateway, including components such as a router and/or other data networking hardware. In some cases, the water in fuel sensing system 304 can be in wireless communication with the location communication device 1208 in order to provide communication with the cloud 1214 or another data network. In some cases, the water in fuel sensing system 304 can receive information from the location communication device 1208 such as geolocation data (which can include latitude/longitude coordinates amongst other things), or other location identifying information such as a nearest address, nearest landmark, etc. As used herein, the term "geolocation data" shall include reference to all location identifying data, unless the context dictates otherwise.

In some cases, geolocation data can be derived from a satellite 1222 based geolocation system. Such systems can include, but are not limited to, GPS L1/L2, GLONASS G1/G2, BeiDou B1/B2, Galileo E1/E5b, SBAS, or the like. In various embodiments, the system can include a geolocation circuit (described below) that can include appropriate signal receivers or transceivers to interface with a satellite 1222 and/or the geolocation circuit can interface with and/or receive data from a separate device or system that provides geolocation data or derives geolocation data from a satellite 1222 or other device. However, it will be appreciated that geolocation data herein is not limited to just that which can be received from or derived from interface with a satellite 1222. Geolocation data can also be derived from addresses, beacons, landmarks, various referential techniques, IP address evaluation, and the like.

In various embodiments, the water in fuel sensing system 304 can also include and/or can be in communication with a mobile communications/guidance device 1210. In some cases, the mobile communications/guidance device 1210 can be used to provide data communication for the water in fuel sensing system 304 and the cloud or another data network. In various embodiments, the mobile communications/guidance device 1210 can provide outputs to or inputs from the vehicle 102 or a driver of the vehicle 102. In some cases, the mobile communications device can be used to provide recommendations (visually, audibly, and/or haptically) to the driver of the vehicle. For example, in various embodiments, a recommendation can be generated by the system and can be forwarded to a mobile communications/guidance device 1210 associated with a vehicle 102 or a driver of a vehicle 102. In various embodiments herein, the system can be configured to generate recommendations for a vehicle 102 driver based on detected water droplets. In various embodiments, the recommendations include at least one of a recommended refueling location, a recommended filter type, a recommended refueling time, and a recommended vehicle service.

Specific recommendations/reports generated by the system can include specific points of information. However, as merely one example, the water in fuel sensing system 304 and/or components thereof can be configured to generate a report relating to different fueling locations (and/or patterns of the same) and the levels of water in fuel of such locations. As another specific example, the water in fuel sensing system 304 and/or components thereof can be configured to generate a report that profiles the frequency with which different drivers in a fleet use recommended and dis-recommended fueling stations.

In some embodiments the mobile communications/guidance device 1210 can be, for example, a smart phone, or another type of computing device including wireless communication capabilities. In some embodiments the mobile communications/guidance device 1210 can be a vehicle navigation system.

In some embodiments, the water in fuel sensing system 304 can also include and/or be in communication with a fleet monitoring center 1224 (real or virtual). The fleet monitoring center 1224 can include a remote computing device 1226 and can receive information and/or recommendation about specific vehicles and/or specific refueling locations. In some cases, the water in fuel sensing system 304 can be used to provide recommendations to a fleet control operator at the fleet monitoring center 1224 and/or receive information or instructions from a fleet control operator at the fleet monitoring center 1224.

In various embodiments, systems described herein can also serve as, or function as, or be a refueling guidance system for a vehicle 102. For example, the water in fuel sensing system 304 and/or components thereof can be configured to query a database 1218 that can include records of specific refueling locations and fuel filter loading rate data related to the specific refueling locations. The water in fuel sensing system 304 can be configured to provide at least one of route and refueling site recommendations to a user output device based on the fuel filter loading rate data.

Figure 13:
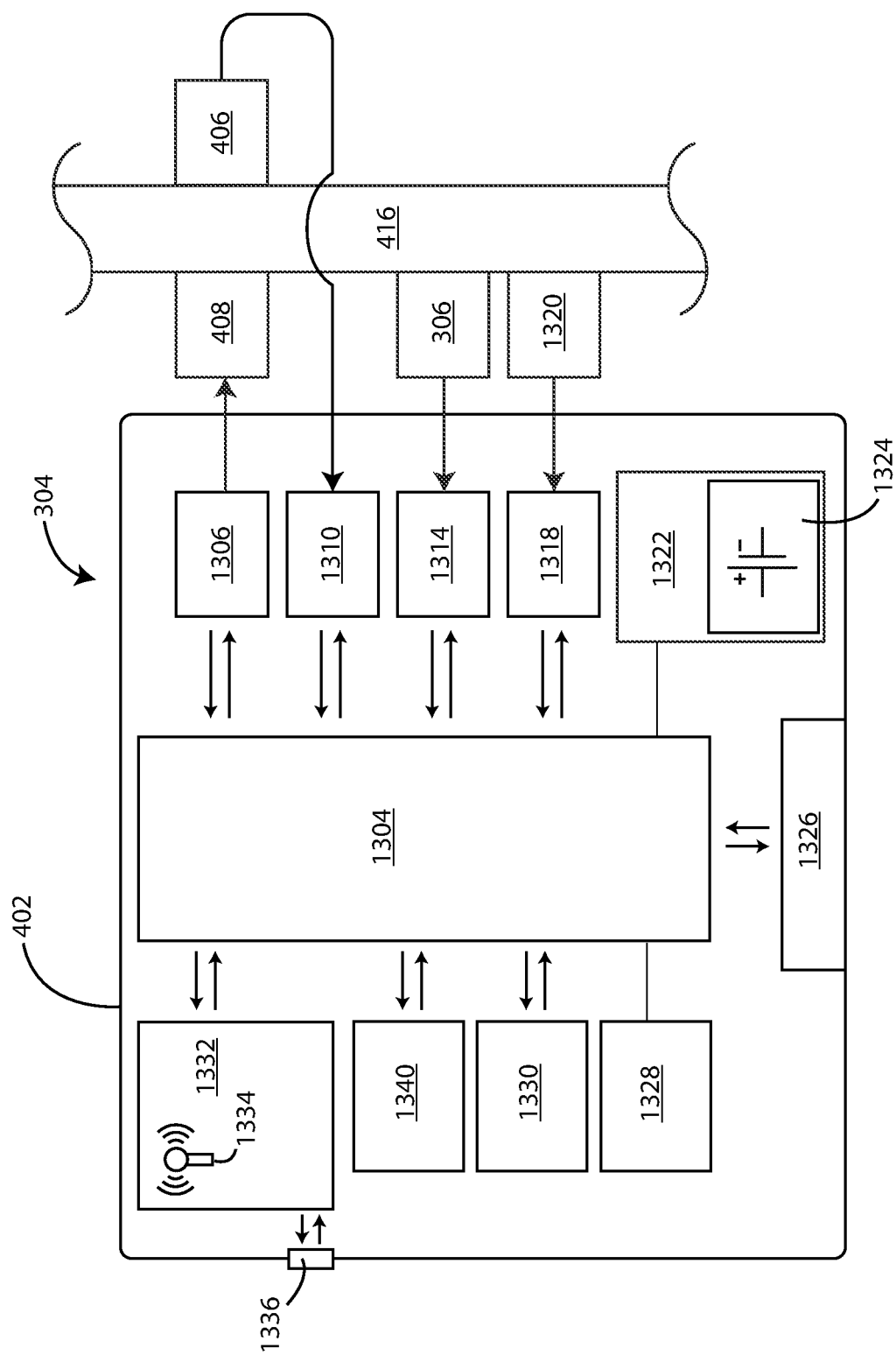
FIG. 13 is a block diagram of components of a water sensing system in accordance with various embodiments herein.

Referring now to FIG. 13, a block diagram of components of a water in fuel sensing system 304 is shown in accordance with various embodiments herein. However, it will be appreciated that a greater or lesser number of components can be included with various embodiments and that this schematic diagram is merely illustrative. The water in fuel sensing system 304 includes a housing 402 and a sensor controller 1304 or ("control circuit" or "system control circuit"). The sensor controller 1304 can include various electronic components including, but not limited to, a microprocessor, a microcontroller, a FPGA (field programmable gate array) chip, an application specific integrated circuit (ASIC), or the like. The sensor controller 1304 can execute various operations as described herein. However, it will be appreciated that operations herein can be executed across multiple devices with separate physical circuits, processors, or controllers with different operations being performed redundantly or divided across different physical devices. As such, some operations may be performed (in whole or in part) at the edge, such as by a circuit/processor/controller associated with a water in fuel sensing system 304 while other operations may be performed (in whole or in part) by a separate device or in the cloud.

The water in fuel sensing system 304 can include a light source 408 and a light detector 406. Both the light source 408 and the light detector 406 can be associated with the flow cell 416. The light source 408 can be in communication with a light source controller 1306. The light detector 406 can be in communication with a light detector channel interface 1310.

In various embodiments, the water in fuel sensing system 304 can include and/or be in communication with a flow rate sensor 306 and a flow sensor channel interface 1314. In various embodiments, the water in fuel sensing system 304 can include and/or be in communication with another type of sensor, such as temperature sensor 1320 and a temperature sensor channel interface 1318. Other types of sensors herein can include vibration sensors, flow sensors, pressure sensors, and the like.

The channel interfaces can include various components such as amplifiers, analog-to-digital converters (ADCs), digital-to-analog converters (DACs), digital signal processors (DSPs), filters (high-pass, low-pass, band-pass) and the like. In some cases, the channel interfaces may not exist as discrete components but, rather, can be integrated into the sensor controller 1304.

Temperature sensors herein can be of various types. In some embodiments, the temperature sensor 1320 can be a thermistor, a resistance temperature device (RTD), a thermocouple, a semiconductor temperature sensor, or the like.

In some embodiments, one or more temperature sensors herein can be configured to measure a temperature of a light source and/or light detector herein. As such, the signal of the light detector can be corrected for temperature effects (e.g., the signal can be normalized). This can be performed in various ways. In one approach, an empirically derived (or otherwise obtained) standard curve or calibration curve relating light output of the light source and/or voltage output of the light detector with temperature can be applied to normalize the signals of the light detector. In some approaches, an equation relating light detector voltage output with temperature over a range of operating temperatures can be used to correct or normalize the signals of the light detector for temperature.

In some embodiments, one or more pressure sensors can also be included herein. Pressure sensors herein can be of various types. The pressure sensors can include, but are not limited to, strain gauge type pressure sensors, capacitive type pressure sensors, piezoelectric type pressure sensors, and the like. In some embodiments, pressure sensors herein can be MEMS-based pressure sensors. In various embodiments, the pressure sensor can be a high-speed (e.g., high sample rate) pressure sensor. In various embodiments the high-speed pressure sensor can sample at rates of 1,000, 1,500, 2,000, 2,500, 3,000, 5,000, 10,000, 15,000, 20,000 Hz or higher, or at a rate falling within a range between any of the foregoing. In various embodiments the high-speed pressure sensor can have a response time of less than 10, 5, 2.5, 1, 0.5, 0.25, 0.1, 0.05 or 0.01 milliseconds, or a response time falling within a range between any of the foregoing.

The processing power of the sensor controller 1304 and components thereof can be sufficient to perform various operations including various operations on signals/data from sensors or other components including, but not limited to averaging, time-averaging, statistical analysis, normalizing, aggregating, sorting, deleting, traversing, transforming, condensing (such as eliminating selected data and/or converting the data to a less granular form), compressing (such as using a compression algorithm), merging, inserting, time-stamping, filtering, discarding outliers, discarding values exceeding a threshold, calculating trends and trendlines (linear, logarithmic, polynomial, power, exponential, moving average, etc.), normalizing data/signals, and the like. Fourier analysis can decompose a physical signal into a number of discrete frequencies, or a spectrum of frequencies over a continuous range. In various embodiments herein, operations on signals/data can include Fast Fourier Transformations (FFT) to convert data/signals from a time domain to a frequency domain. Other operations on signals/data here can include spectral estimation, frequency domain analysis, calculation of root mean square acceleration value ($G_{RMS}$), calculation of acceleration spectral density, power spectral densities, Fourier series, Z transforms, resonant frequency determination, harmonic frequency determination, and the like. It will be appreciated that while various of the operations described herein (such as Fast Fourier transforms) can be performed by general-purpose microprocessors, they can also be performed more efficiently by digital signal processors (DSPs) which can, in some embodiments, be integrated with the sensor controller 1304 or may exist as separate, discrete components.

In various embodiments, the water in fuel sensing system 304 can include a power supply circuit 1322. In some embodiments, the power supply circuit 1322 can include various components including, but not limited to, a battery 1324, a capacitor, a power-receiver such as a wireless power receiver, a transformer, a rectifier, and the like.

In various embodiments the water in fuel sensing system 304 can include an output device 1326. The output device 1326 can include various components for visual and/or audio output including, but not limited to, lights (such as LED lights), a display screen, a speaker, and the like. In some embodiments, the output device can be used to provide notifications or alerts to a system user such as current system status, an indication of a problem, a required user intervention, a proper time to perform a maintenance action, or the like.

In various embodiments the water in fuel sensing system 304 can include memory 1328 and/or a memory controller. The memory can include various types of memory components including dynamic RAM (D-RAM), read only memory (ROM), static RAM (S-RAM), disk storage, flash memory, EEPROM, battery-backed RAM such as S-RAM or D-RAM and any other type of digital data storage component. In some embodiments, the electronic circuit or electronic component includes volatile memory. In some embodiments, the electronic circuit or electronic component includes non-volatile memory. In some embodiments, the electronic circuit or electronic component can include transistors interconnected to provide positive feedback operating as latches or flip flops, providing for circuits that have two or more metastable states, and remain in one of these states until changed by an external input. Data storage can be based on such flip-flop containing circuits. Data storage can also be based on the storage of charge in a capacitor or on other principles. In some embodiments, the non-volatile memory 1328 can be integrated with the sensor controller 1304.

In various embodiments the water in fuel sensing system 304 can include a clock circuit 1330. In some embodiments, the clock circuit 1330 can be integrated with the sensor controller 1304. While not shown in FIG. 13, it will be appreciated that various embodiments herein can include a data/communication bus to provide for the transportation of data between components such as an $I^2C$, a serial peripheral interface (SPI), a universal asynchronous receiver/transmitter (UART), or the like. In some embodiments, an analog signal interface can be included. In some embodiments, a digital signal interface can be included.

In various embodiment the water in fuel sensing system 304 can include a communications circuit 1332. In various embodiments, the communications circuit can include components such as an antenna 1334, amplifiers, filters, digital to analog and/or analog to digital converters, and the like. In some embodiments, the water in fuel sensing system 304 can also include wired input/out interface 1336 for wired communication with other systems/components including, but not limited to one or more vehicle ECUs, a CANBus network, or the like.

The fuel monitoring system for a vehicle can also include a geolocation circuit 1340. In various embodiments, the geolocation circuit 1340 can be configured to generate or receive geolocation data. In various embodiments, the geolocation circuit 1340 can receive geolocation data from a separate device. In various embodiments, the geolocation circuit 1340 can infer geolocation based on detection of a wireless signal (such as a WIFI signal, a cell tower signal, or the like). In various embodiments, the geolocation circuit 1340 can include a satellite communications circuit.

The system and/or the sensor controller 1304 can be configured to make various calculations as described herein. For example, in various embodiments, the sensor controller 1304 can, using inputs as described herein, be configured to estimate the amount of water in fuel. It will be appreciated that references to water in fuel herein shall refer to free water in fuel unless the context dictates otherwise. Many other calculations that can be executed by the sensor controller 1304 and/or other components of the system are described in greater detail below.

Estimating Amount of Water in Fuel

As described herein, the system can be configured to estimate the amount of water in fuel. Such estimates can be based on various inputs or estimates including one or more of the number of water droplets detected per unit time (N), the average size/volume of water droplets detected (V), the flow rate of fuel through the sensor (F), and the like. In one approach, the amount of water in fuel (WIF) can be estimated and described as the fraction of water in fuel according to the following equation:

$$WIF = \frac{N * V}{F}$$

The number of water droplets detected per unit time can be directly detected by the sensor(s) of a water in fuel sensing system herein as described and as illustrated with respect to the examples below.

The size/volume of water droplets detected can be estimated as described above based on the optical signals such as described with respect to FIGS. 5-10.

The flow rate of fuel can be measured/determined/estimated in various ways. In some embodiments, the system can include a flow rate sensor producing a value for flow rate of fuel. In some embodiments, the system can receive data on fuel flow rate from a vehicular data network, such as CANBus or the like.

In some embodiments, a value for flow rate can be estimated using the Bernoulli equation and information regarding the pressure drop between two points. In specific, a relationship between flow rate and pressure drop exist that can be used in order to estimate a flow rate. Thus, in some embodiments, herein measures of pressure upstream and downstream from where the water droplets are detected can be used to estimate the flow rate of fuel. In some embodiments, the relationship between pressure drop and flow rate can be determined empirically and then programmed into the system or a component thereof.

In some embodiments, a relationship between pressure drop and flow rate through a flow cell or fuel line herein can be determined empirically for water and then modified for use with diesel fuel. By way of example, the following equation can be used where values P1 and P2 are determined empirically for water, and where $P_{S,F}$ is the pressure drop across the sensor when the fluid is fuel, $\mu_W$ and $\mu_F$ are the dynamic viscosities of water (1 cP) and diesel fuel (~2.5 cP) respectively, and $U_{S,W}$ is the fuel flow rate through the sensor:

$$P_{S,F} = \frac{\mu_W}{\mu_F} P_{S,W} = \frac{\mu_W}{\mu_F}(P1 * U_{S,F} - P2)$$

In some embodiments, a relationship can exist between the total number of water droplets detected per unit time as normalized by a flow rate of fuel and the amount of water in the fuel. As such, in some embodiments, data regarding the number of droplets detected by the sensor(s) of a water in fuel sensing system herein can be combined with data regarding a flow rate of fuel in order to generate an estimate of the amount of water in the fuel.

It will be appreciated that there can be significance associated with whether a level of water is merely short-term (acute) or long-term (chronic). This significance can apply to determining possible sources of water contamination in fuel as well as the relative risk of damage to the vehicle posed. For example, if a high level of water in fuel exists only acutely, then this may point to a cause such as a recent refueling event at a particular location. In contrast, if a high level of water in fuel is detected chronically, then this may point to a cause intrinsic to the vehicle itself and warrant maintenance work to be performed on the vehicle.

There can also be significance associated with patterns (time, geography, etc.) of detected amounts of water in fuel. For example, if a high level of water in fuel is detected every morning then this may point to a cause such as ending the day with an empty fuel tank, which can result in condensation forming in the fuel tank and getting into the fuel.

In various embodiments herein, machine learning algorithms can be used to derive patterns between estimated amounts of water in fuel and other pieces of information available to the system including, but not limited to, geolocation of refueling locations, time of refueling events, ambient temperature, ambient humidity, weather conditions, vehicle operator identity, routes traveled, and the like.

Machine learning algorithms used herein can include, but are not limited to, supervised learning and unsupervised learning algorithms. Machine learning algorithms used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Machine learning algorithms herein can also include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms herein can include categorical mixture models, deep learning methods, hierarchical clustering, K-means clustering, correlation clustering, and kernel principal component analysis. Ensemble learning algorithms herein can include boosting, bootstrap aggregating, ensemble averaging, and mixture of experts. General algorithms for predicting arbitrarily structured sets of labels herein can include Bayesian networks and Markov random fields. Multilinear subspace learning algorithms herein can include multilinear principal component analysis (MPCA). Real-valued sequence labeling algorithms can include Kalman filters and particle filters. Regression algorithms herein can include both supervised (such as Gaussian process regression, linear regression, neural networks and deep learning methods) and unsupervised (such as independent component analysis and principal components analysis) approaches. Sequence labeling algorithms herein can include both supervised (such as conditional random fields, hidden Markov models, maximum entropy Markov models, and recurrent neural networks) and unsupervised (hidden Markov models and dynamic time warping) approaches.

In some embodiments, various actions/operations of the system can be triggered by an estimated amount of water crossing a threshold value. In some embodiments, these threshold values can be predetermined and/or fixed. In other embodiments, these threshold values can be dynamic.

In some embodiments, the system can distinguish between an estimated amount of water in fuel creating a need to stop vehicle operation immediately versus an estimated amount of water in fuel allowing continued operation. In one example, distinguishing between these different categories can be performed according to threshold values. One example of an implementation of this approach is provide below in Table 1. However, it will be appreciated that many variations are contemplated herein.

TABLE 1

| Estimated Water in Fuel Level | Recommended Action |
|---|---|
| <200 ppm | No Action Required |
| 200 to <500 ppm | Recommend Maintenance for Fuel Filter at Next Stop |
| >500 ppm | Recommend Stopping Vehicle Operation Immediately for Maintenance |

Different categories of estimated water amounts can also be reflected in qualitative notifications sent to a vehicle operator, a fleet controller, or another person or system. For example, in some embodiments, a notification can be sent that can reflect either a "high", "medium", or "low" amount of estimated water in fuel. One example of this is provided in Table 2 below, however this is merely one example and many other specific categories and values are contemplated herein.

TABLE 2

| Estimated Water in Fuel Level | Qualitative Category |
|---|---|
| <200 ppm | Low |
| 200 to <500 ppm | Medium |
| >500 ppm | High |

In some embodiments, the threshold values may be different depending on whether the estimated amount of water is only short term (acute or transitory) versus long-term (chronic). In various embodiments, the threshold values may be higher for short term values versus long term values. One example of how threshold values might be different based on short-term or long-term amounts is shown below in Table 3. However, this is merely one example and many other threshold values are contemplated herein.

TABLE 3

| Estimated Water in Fuel Level | | Qualitative |
| Short-Term | Long-Term | Category |
|---|---|---|
| <250 ppm | <200 ppm | Low |
| 250 to <600 ppm | 200 to <500 ppm | Medium |
| >600 ppm | >500 ppm | High |

In some embodiments, specific threshold values can vary from those shown above in tables 1-3. For example, in some embodiments, actual threshold values can be about 10, 20, 30, 40, 50, 60, 70, 80, 100, 150, 200, 250, or 300 ppm greater or lesser than the specific values shown in tables 103.

Mitigating Effect of Air Bubbles

In some instances, air bubbles may be present in a fuel line of a fuel system. It has been found herein that since air has a different refractive index than fuel, light can be scattered and reflected off the interface (between fuel and an air bubble) or otherwise transmitted and refracted through the interface. This leads to less light reaching the sensor detector and gives the appearance of a light absorbance event. Therefore, air bubbles can also generate what appear to be absorbance peaks and therefore can potentially be confused with water droplets making the presence of air bubbles a potential source of error when measuring water concentration in a fuel line.

However, various embodiments herein can be configured to prevent the presence of air bubbles from interfering with the measurement of water droplets in fuel. In some embodiments, signal processing approaches can be used to distinguish between water droplets and air bubbles. In specific, air bubbles have been found to generate what appear to be absorbance peaks of greater absorbance magnitude and peak width. As such, signal processing techniques can be used in accordance with systems herein to prevent the presence of air bubbles from interfering with the measurement of water droplets in fuel. For example, in some embodiments, the system can be configured to exclude peaks crossing a threshold value for absorbance magnitude and/or peak width when calculating the amount of water in fuel. The threshold value can be an absolute value or a relative value. In some embodiments, the threshold value can be a statistical measure such as an average value, a standard deviation value of a distribution, a percentile value, or the like.

Other techniques can also be used to mitigate the effects of air bubbles on the measurement of water in fuel. In some embodiments, a secondary detector can be used to determine an amount of light reflected which distinguishes between water droplets and air bubbles. For example, in some embodiments herein, the fluid handling portion of the sensor can be configured to exclude air bubbles from reaching the sensing channel. In some embodiments, the system can be configured to measure absorbance at two different wavelengths of light (for example, using a first light source configured to emit near-infrared light and a second light source configured to emit light within the visible spectrum) and distinguish between water droplets and air bubbles by comparing the absorbance peaks generated at one wavelength versus the other.

Figure 23:
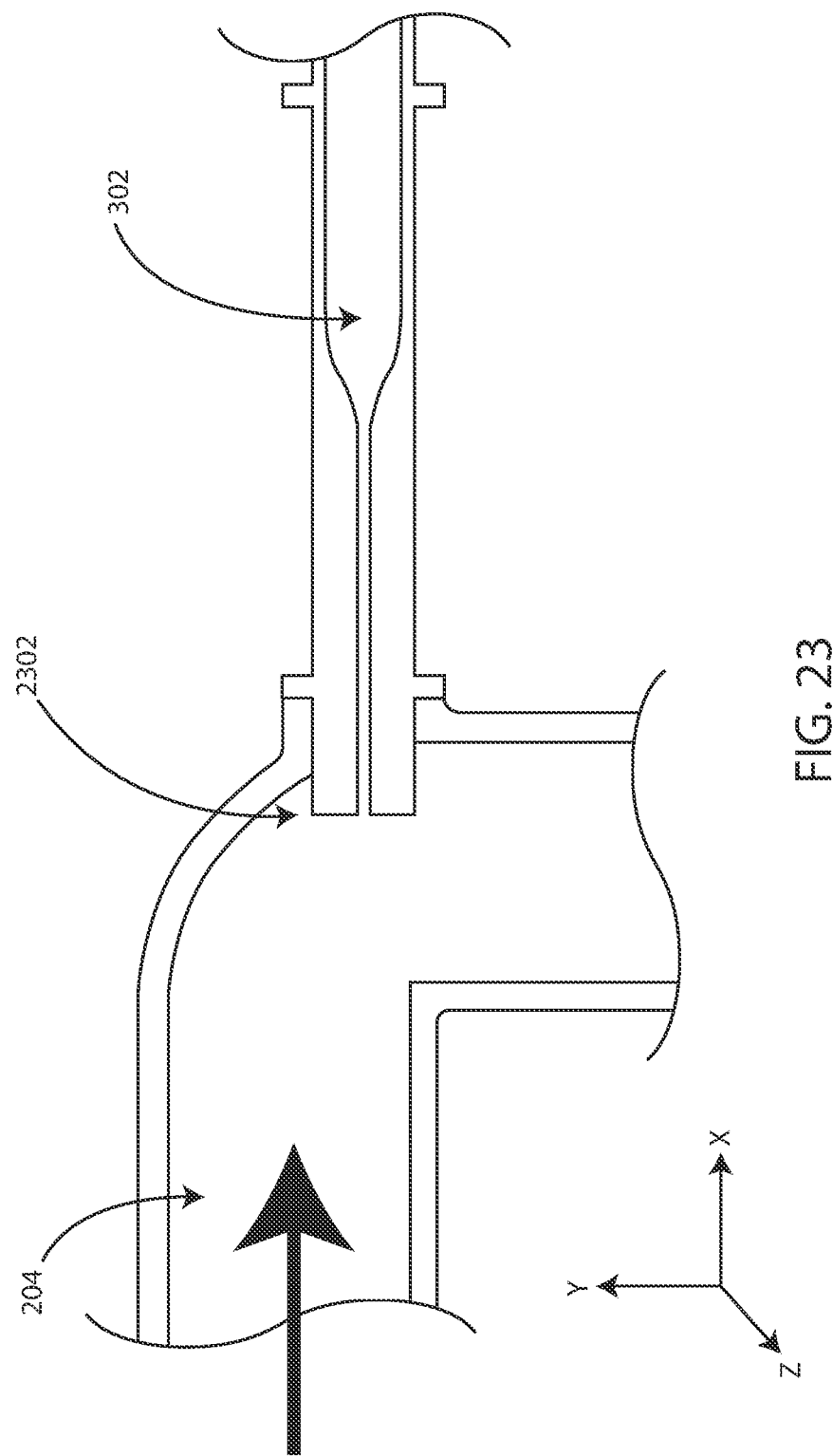
FIG. 23 is diagram showing key fluidic pathways of a sensing system herein.

In some embodiments, the components of the system can be arranged such that the buoyancy of air bubbles prevents them from entering the sensor. Referring now to FIG. 23, a diagram is shown illustrating key fluidic pathways of a sensing system herein. FIG. 23 shows fuel line 204 along with sampling channel inlet 2302 and flow channel 302 (or sampling channel). The components can be disposed such that buoyancy of the air bubbles does not promote their entry into the inlet 2302. For example, the components can be arranged such that gravity is in direction Z. This can lead to a reduced amount of air bubbles entering the inlet 2302.

Figure 24:
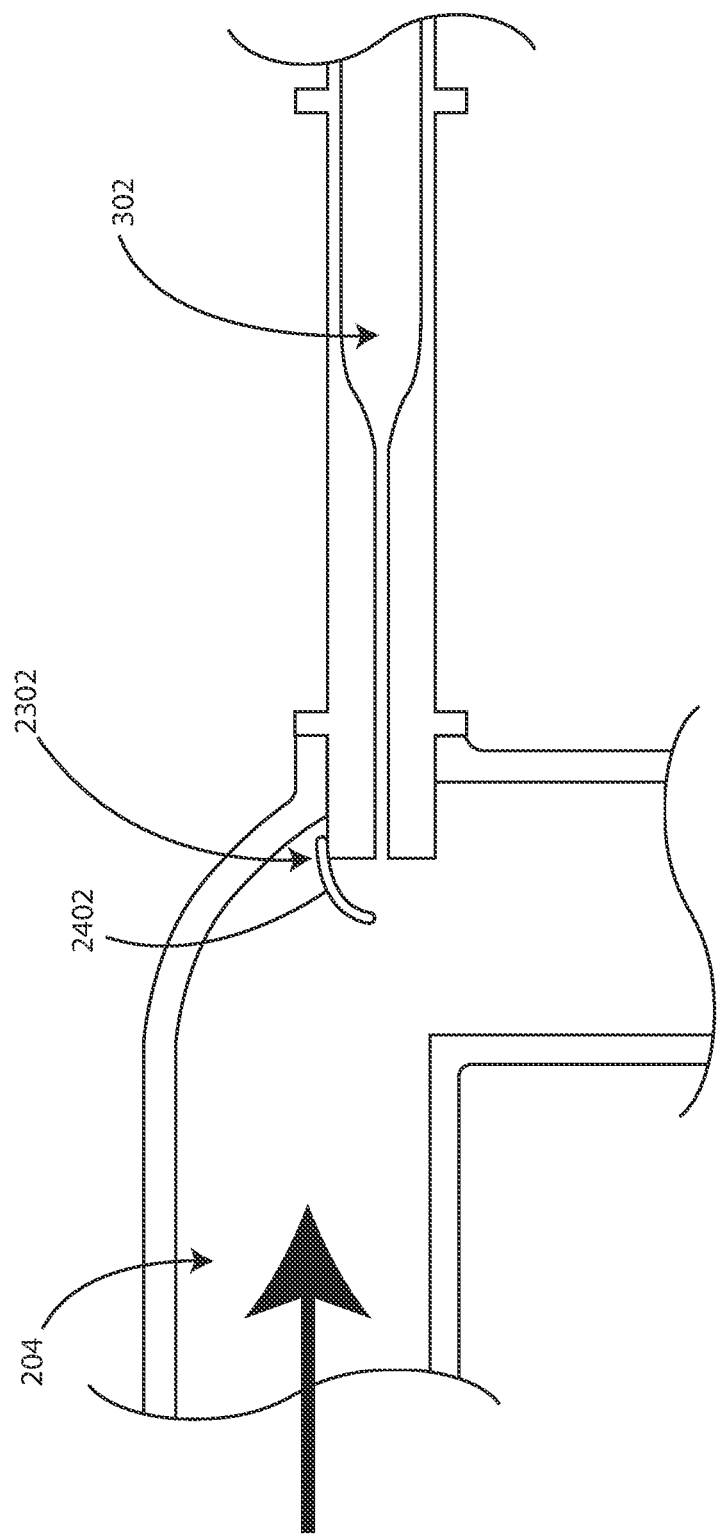
FIG. 24 is diagram showing key fluidic pathways of a sensing system herein.

In some embodiments, a shield can be used to prevent air bubbles from entering the sensor. FIG. 24 is a diagram showing key fluidic pathways of a sensing system herein and is generally similar to FIG. 23. In the example of FIG. 24, the system can include a shield 2402 positioned to prevent air bubbles from entering into the inlet 2302. In some embodiments, the shield can take the form of a solid piece of material. In some embodiments, the shield can take the form of a screen or porous material that prevents air, but not liquids, from passing therethrough. In some embodiments, the shield can be positioned to partially block a pathway to the inlet 2302. In some embodiments, such as with a screen or porous material, the shield can be positioned to entirely block a pathway to the inlet 2302.

Figure 25:
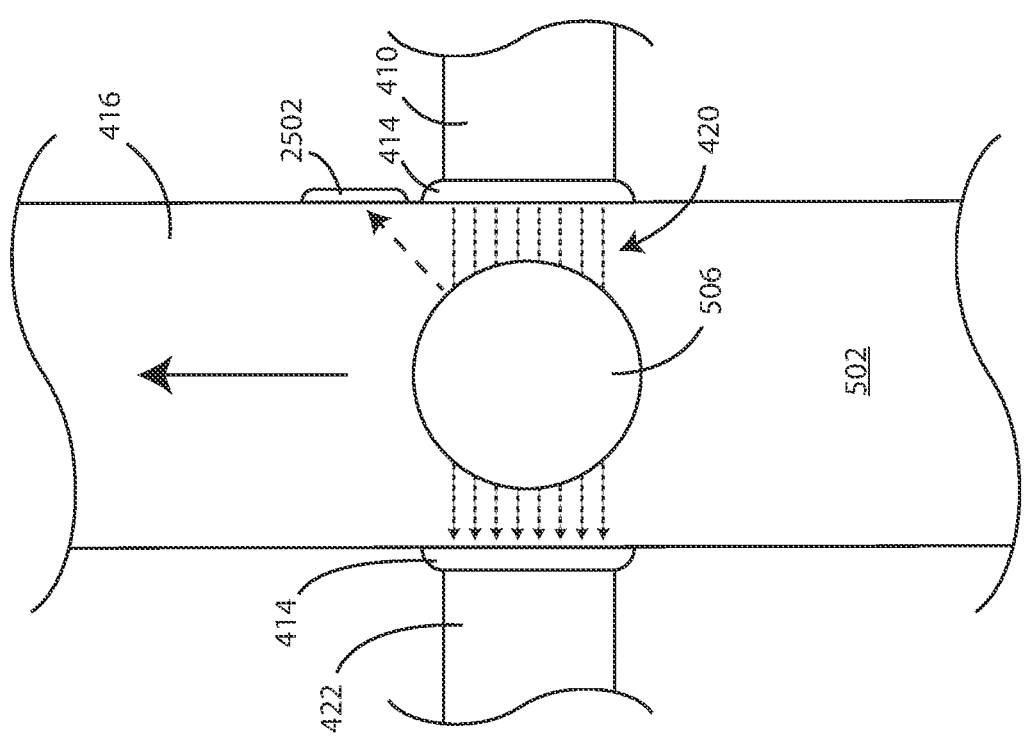
FIG. 25 is a schematic view of a portion of a water sensing system in accordance with various embodiments herein.

In some embodiments, a secondary detector can be used to determine an amount of light reflected which distinguishes between water droplets and air bubbles. Referring now to FIG. 25, a schematic view is shown of a portion of a water sensing system in accordance with various embodiments herein. FIG. 25 is generally similar to FIG. 5 described above. However, in this embodiment, a secondary detector 2502 is included and is positioned to be able to detect reflected light from air bubble passing through the sensor.

Methods

Many different methods are contemplated herein, including, but not limited to, methods of monitoring water contamination in fuel, methods of monitoring vehicle operation, and the like. Aspects of system/device operation described elsewhere herein can be performed as operations of one or more methods in accordance with various embodiments herein.

In an embodiment, a method of monitoring water contamination in a vehicular fuel line is included, the method can include operations of emitting light with a light source into a microfluidic channel in fluid communication with the fuel line, receiving light from the microfluidic channel with a light detector, evaluating signals received from the light detector with a sensor controller, identifying water droplets based on a deviation in the signals received from the light detector from a baseline level, generating an estimate of the amount of water in a fuel based on the identified water droplets, and initiating generation of a notification if the estimated amount of water exceeds a threshold value.

In an embodiment, the method can further include estimating the size of identified water droplets based in part on an increase and a successive decrease in the light received by the light detector with respect to a baseline level.

In an embodiment, the method can further include generating an estimate of the amount of water in a fuel based on the number of identified water droplets per unit time and estimates of the size of the identified water droplets.

In an embodiment, the method can further include initiating generation of a first notification if the estimated amount of water exceeds a first threshold value and a second notification if the estimated amount of water exceeds a second threshold value.

In an embodiment, the method can further include initiating generation of a vehicle driver notification regarding the estimated amount of water. In an embodiment of the method, the vehicle driver notification classifies the estimated amount of water as one of normal, above normal, and requiring immediate action. In an embodiment of the method, the vehicle driver notification classifies the estimated amount of water as one of normal, above normal, and requiring immediate action, as distinguished by acute and chronic water levels. In an embodiment of the method, the threshold comprises a first threshold for chronic water amounts and a second threshold for acute water amounts.

Aspects may be better understood with reference to the following examples. These examples are intended to be representative of specific embodiments but are not intended as limiting the overall scope of embodiments herein.

EXAMPLES

Example 1: Detection of Water in Fuel

A water in fuel sensing system was set up consistent with that shown in FIG. 3. In specific, the light source was a near-infrared light emitting diode operating at a wavelength of 1550 nm and the light detector was germanium (Ge) based photodiode sensor with an active area of 3 mm in diameter (7.1 mm$^2$). A first optical fiber (400 μm core fiber diameter) was used to connect the light source to a glass flow cell formed of borosilicate glass and having an internal diameter for 205 μm at the sampling location. The first optical fiber was adhered to the flow cell using an optical adhesive (Norland NOA63). A second optical fiber (200 μm core fiber diameter) was disposed on the opposite side of the flow cell and adhere thereto using the optical adhesive.

Figure 14:
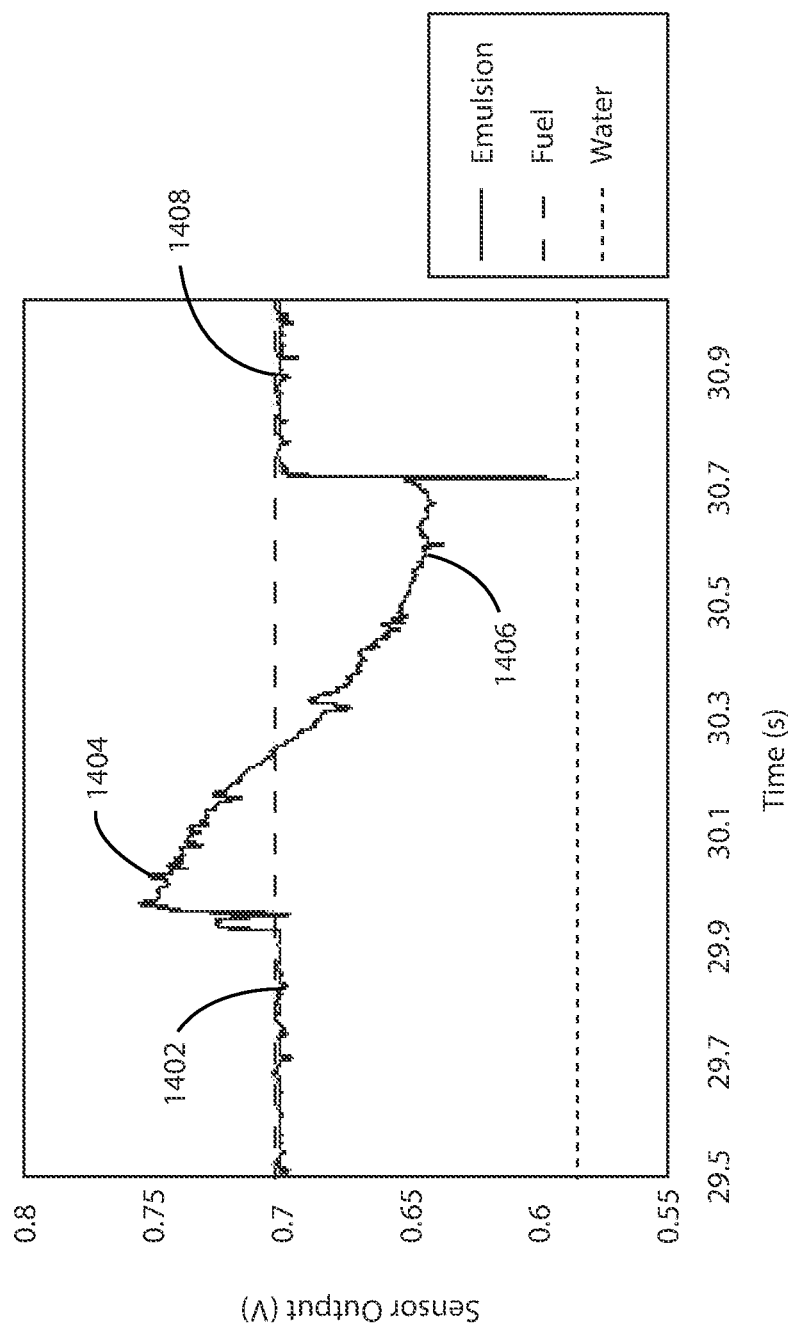
FIG. 14 is a view of potential versus time for a sensing system in accordance with various embodiments herein.

Water was introduced into a fuel sample which was then passed through the flow cell. The signal from the light detector was recorded. FIG. 14 is the signal for a single droplet passing through the flow channel. The long dashed horizontal line represents an averaged value for a pure fuel-filled flow cell and the short dashed horizontal line represents the signal for a water-filled channel. FIG. 14 shows that water droplets of a sufficient size can be detected by observing a baseline signal value 1402 followed by an increased signal value 1404 followed by a decreased signal value 1406, followed by a return to the baseline signal value 1408.

Figure 15:
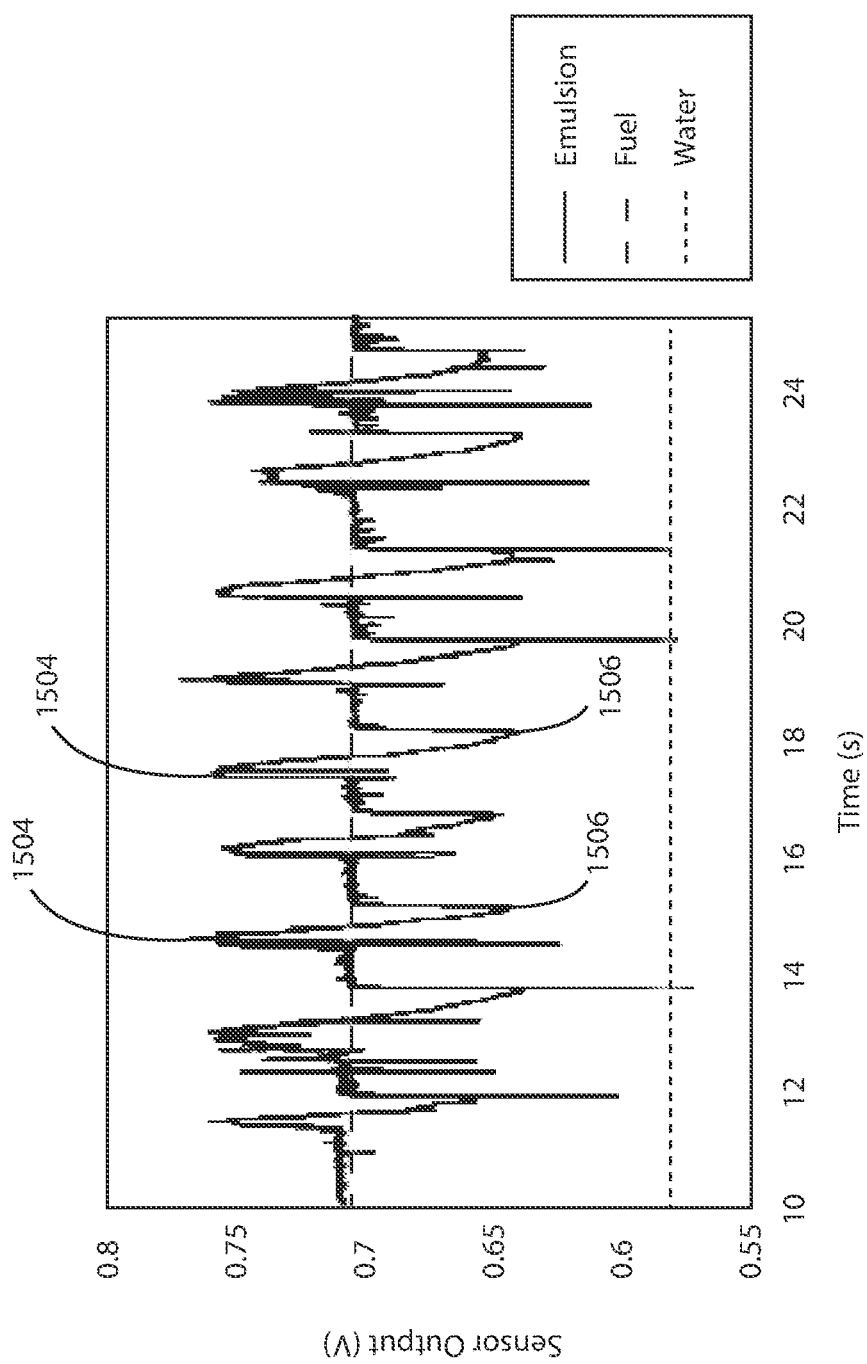
FIG. 15 is a view of potential versus time for a sensing system in accordance with various embodiments herein.

An emulsion (plurality of water droplets) was formed and then sent through the flow cell. FIG. 15 shows the sensor output as the emulsion passes through overlaid with an averaged value for a pure fuel-filled flow cell (long-dashed line) and water-filled channel (short-dashed line). Peaks 1504 and valleys 1506 are clearly observed as water drops pass through the sensing area. This shows that a system herein can be used to obtain a count of water droplets over time.

Example 2: Water Drop Size Distribution Differences

A water in fuel sensing system was set up consistent with that shown in FIG. 3. In specific, a sensing system was prepared with a 300 um ID borosilicate glass flow cell. The light source was a near-infrared LED (1550 nm; Thor Labs) and was focused on the channel with a 200 um fiber optic cable (Thor Labs). The light was detected with a variable gain InGaAs detector set at 60 dB of gain (Thor Labs). Light was collected and delivered to the detector with a 400 um fiber optic cable. The flow cell was encased in a machined aluminum body, designed to sample a portion of the main flow.

The sensor was placed on a fuel-water separation test bench typically used for testing water removal filters according to standard methods. Water drop distributions (d50=45

μm, 75 μm, 90 μm and 125 μm) (d50 is the diameter at which 50% of the volume is contained in droplets smaller than that diameter) were generated and sent to the sensor with varying water concentrations. The main flow operated at 4 L/min and consisted of diesel fuel. The flowrate through the flow cell was approximately 1 mL/min.

Signal data was captured with a data acquisition system. Signal processing and peak identification was completed in MATLAB using standard peak fitting algorithms.

Figure 16:
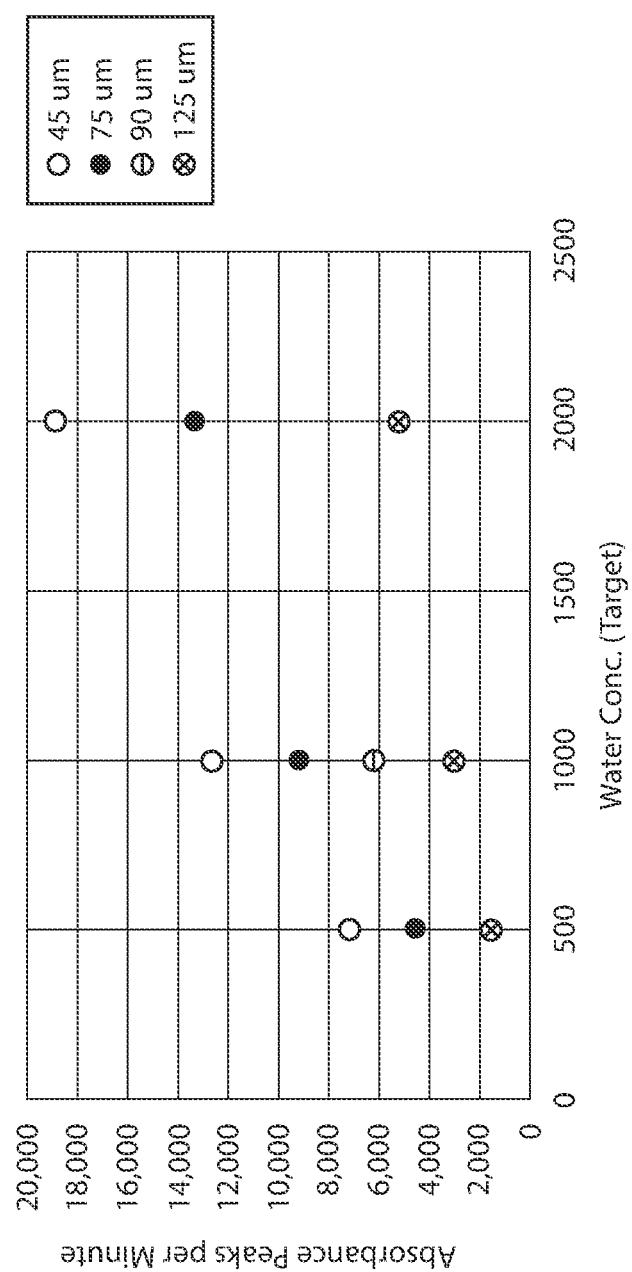
FIG. 16 is a graph showing absorbance peaks per minute vs. water concentration for different size distributions of water droplets.
Figure 17:
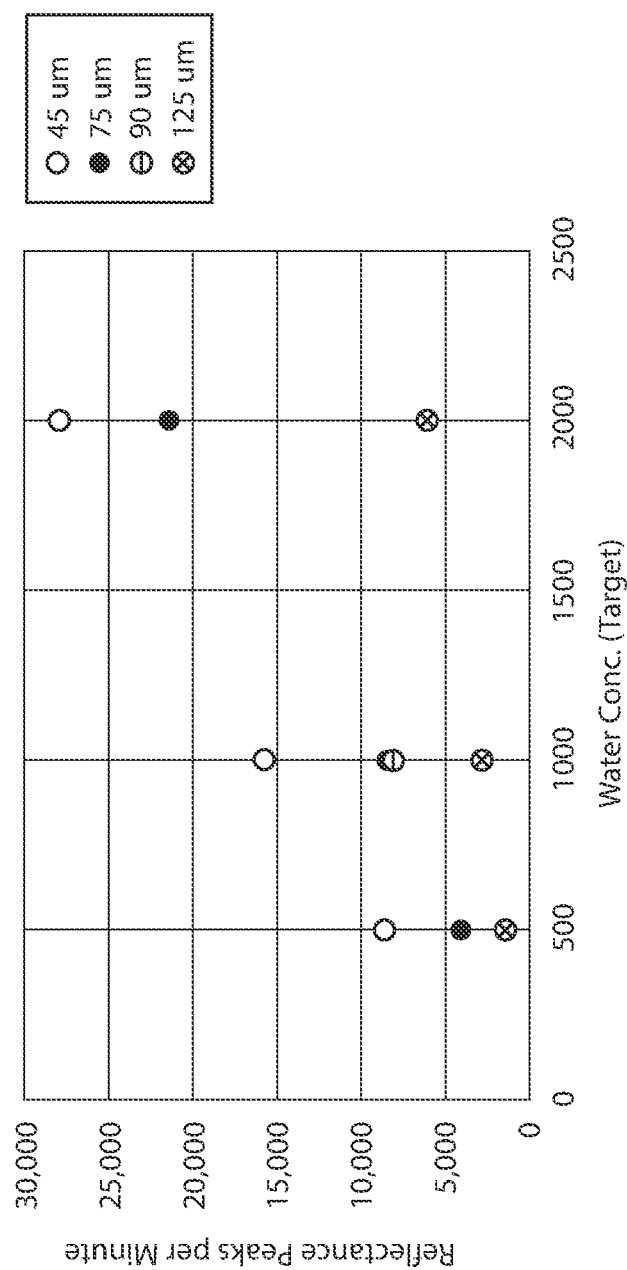
FIG. 17 is a graph showing reflection peaks per minute vs. water concentration for different size distributions of water droplets.

FIG. 16 is a graph showing absorbance peaks per minute vs. water concentration for different size distributions of water droplets (45 μm, 75 μm, 90 μm and 125 μm), wherein absorbance is calculated as common logarithm of the ratio of incident to transmitted radiant power through the flow cell. This shows that the relationship between absorbance peaks versus water concentration is very linear. FIG. 17 is a graph showing reflection peaks per minute vs. water concentration for different size distributions of water droplets (45 μm, 75 μm, 90 μm and 125 μm).

Figure 18:
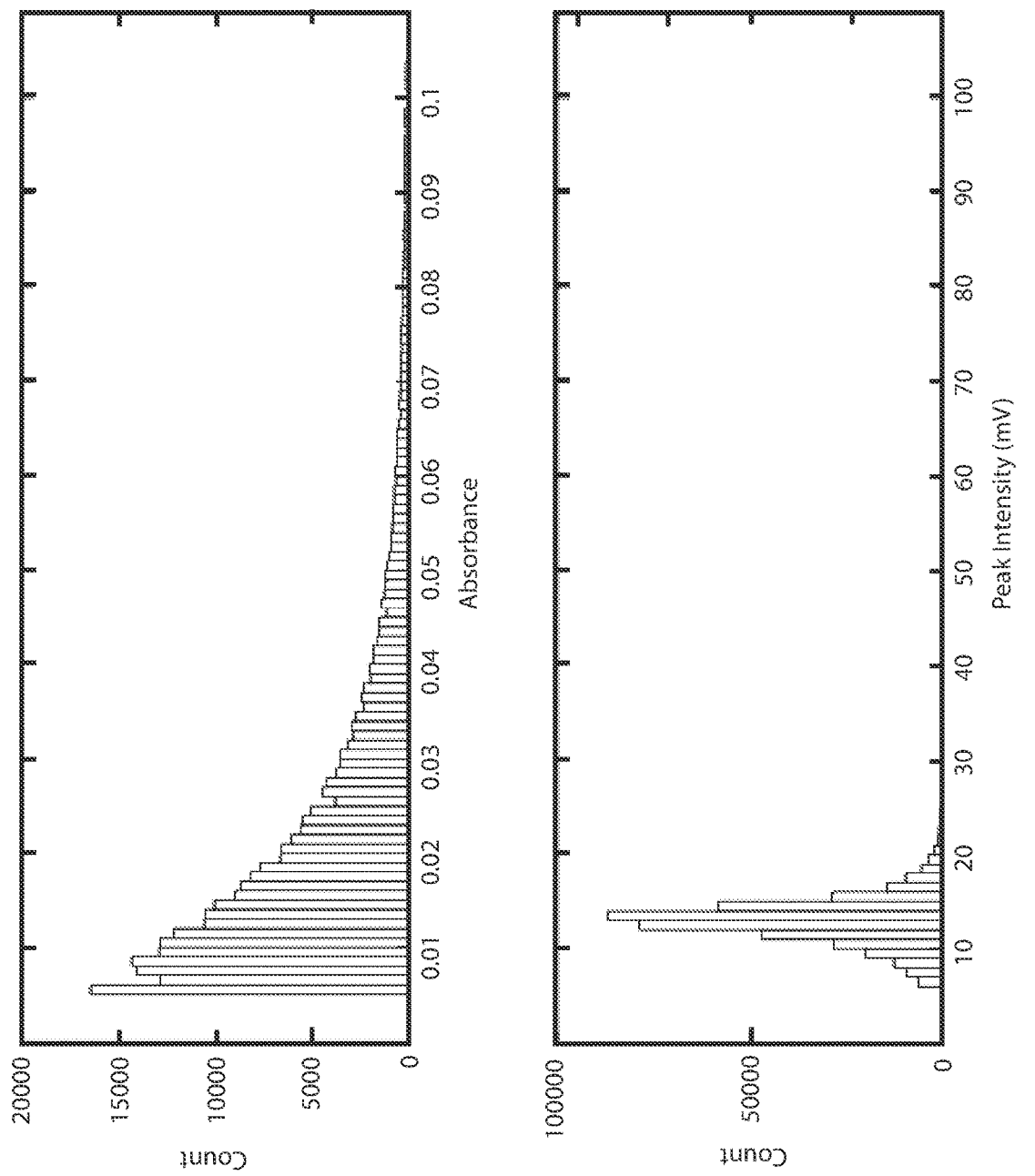
FIG. 18 is a histogram of absorbance values and a histogram of peak intensity values for a size distribution of water droplets.
Figure 19:
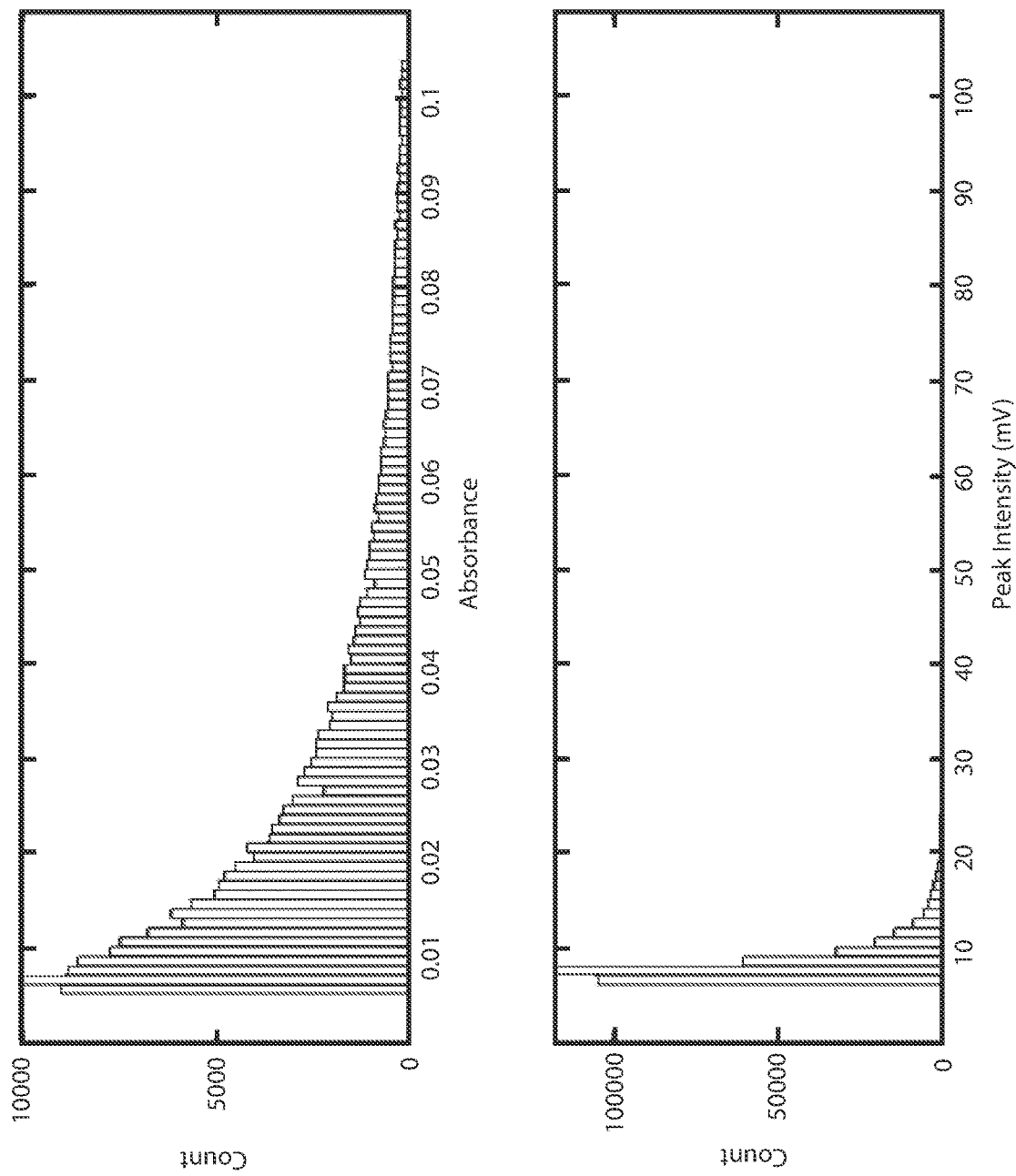
FIG. 19 is a histogram of absorbance values and a histogram of peak intensity values for a size distribution of water droplets.
Figure 20:
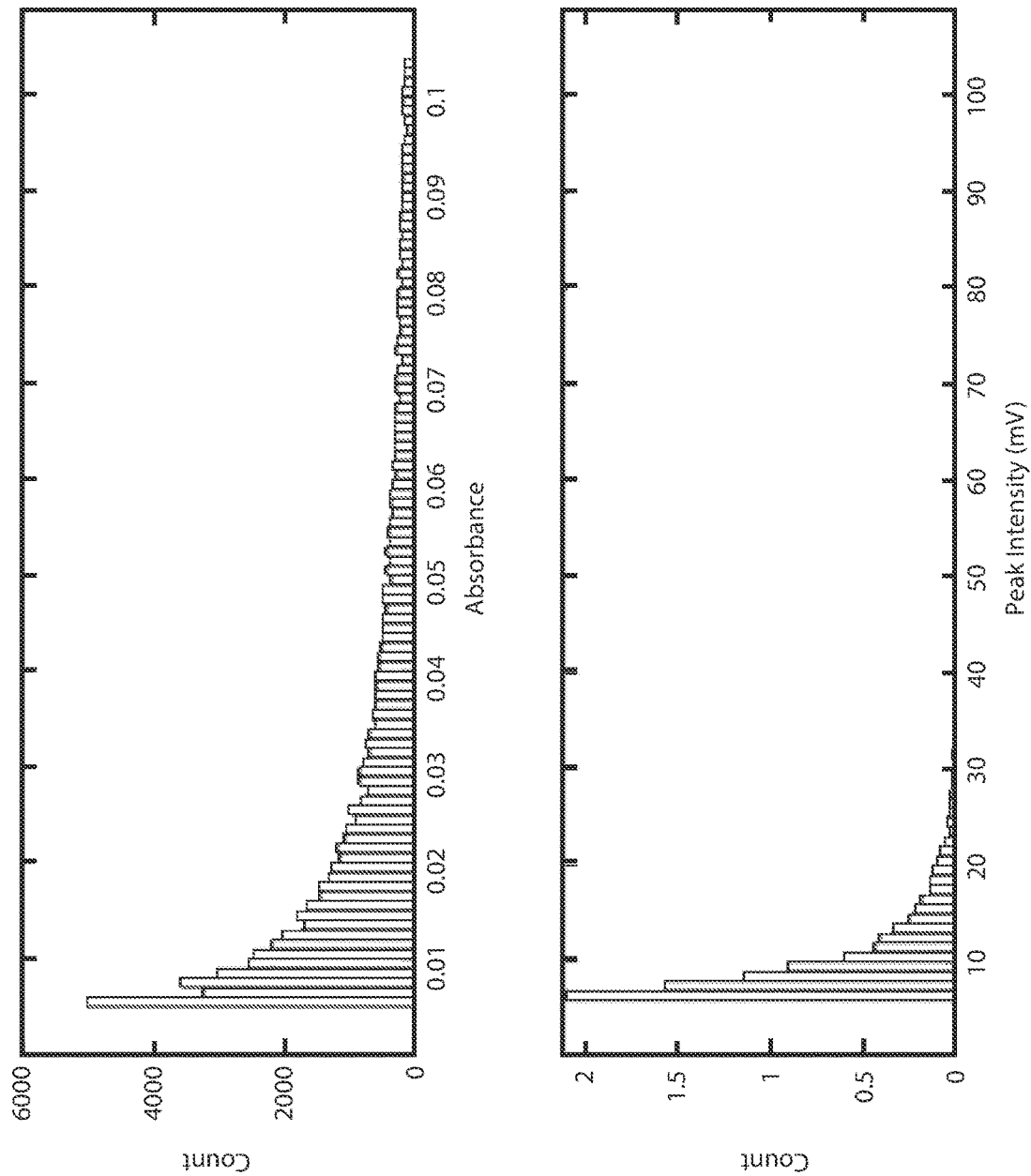
FIG. 20 is a histogram of absorbance values and a histogram of peak intensity values for a size distribution of water droplets.

FIG. 18 is a histogram of absorbance values and a histogram of peak intensity values for a size distribution of water droplets (d50=45 μm). FIG. 19 is a histogram of absorbance values and a histogram of peak intensity values for a size distribution of water droplets (d50=75 μm). FIG. 20 is a histogram of absorbance values and a histogram of peak intensity values for a size distribution of water droplets (d50=125 μm). This example shows that smaller droplet distributions have a greater % of small absorbances. This example also shows that larger droplet distributions have more larger absorbances. Further, this example shows that the shape of the 'reflection' histogram also gives information on droplet size distribution. Larger drops reflect light better than smaller drops. Thus, evaluation of data can allow for the size distribution of droplets to be determined in a flow of fuel.

Example 3: Size Limit of Detection

The sensor droplet size limit of detection (e.g., the minimum size of a droplet to create a peak in the sensor signal) was determined using an approach based on comparing observed peak count ratios between two experiments and expected peak count ratio for different limit of detections. In specific, comparing experiments of d50=45 μm and d50=125 μm (both at 500 ppm) it was found that the ratio of peak frequency or number is 2.895 (i.e. the d50=45 μm has 2.895 as many peaks as the d50=125 μm).

Figure 21:
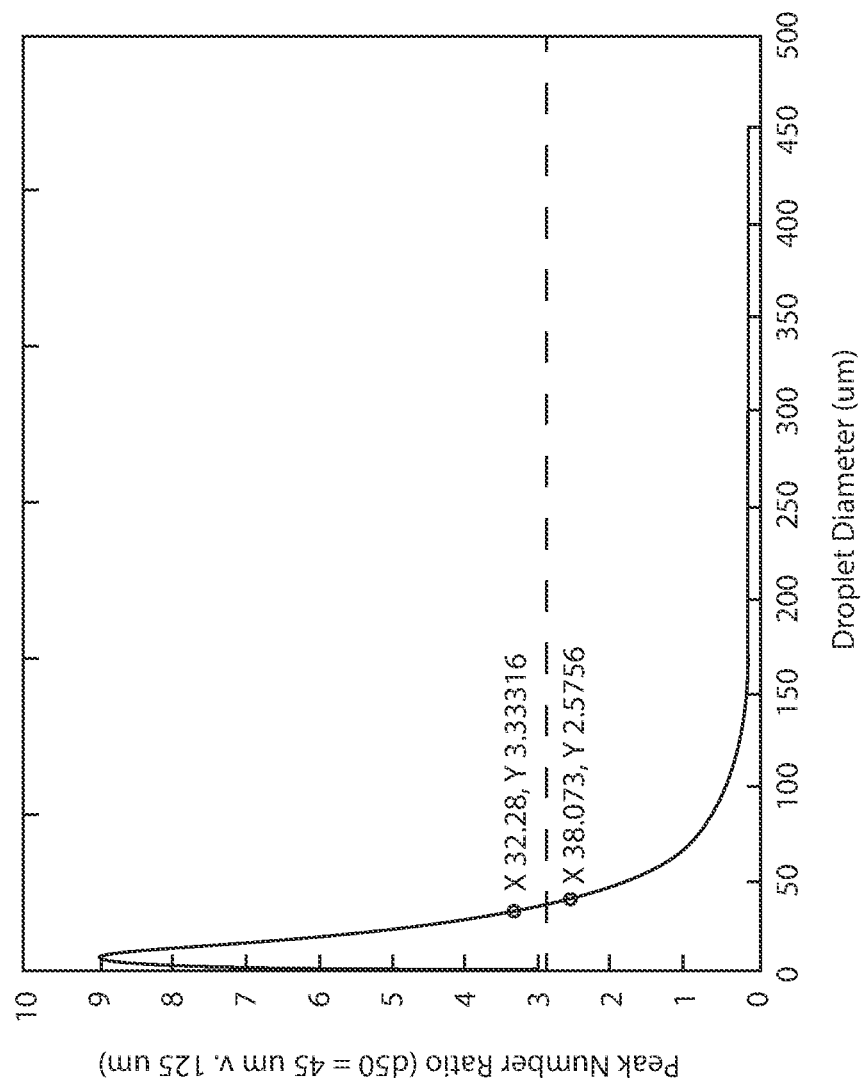
FIG. 21 is a graph showing peak number ratio between two different droplet size distributions versus droplet diameter.

Authoritative data for water volume vs. droplet size was obtained using a Malvern Insitec laser diffraction particle sizing system. The volumetric data from the Malvern was converted to number data to determine the expected droplet frequency ratio for a given theoretical limit of detection (Table 4 and FIG. 21).

TABLE 4

| Theoretical Limit of Detection (gm) | Expected Droplet Frequency Ratio |
|---|---|
| 10.17 | 8.417 |
| 11.99 | 7.915 |
| 14.14 | 7.434 |
| 16.68 | 6.633 |
| 19.67 | 5.881 |
| 23.20 | 4.997 |
| 27.37 | 4.180 |
| 32.28 | 3.333 |
| 38.07 | 2.576 |

TABLE 4-continued

| Theoretical Limit of Detection (gm) | Expected Droplet Frequency Ratio |
|---|---|
| 44.91 | 1.965 |
| 52.97 | 1.473 |

Thus, based on an observed ratio of peak frequency of 2.895, the limit of detection in this example was between 32.28 and 38.07 μm. It will be appreciated that this example is merely illustrative of a technique of determining a limit of detection and that various embodiments herein are capable of lower limits of detection such as approximately 30 μm, 27.5 μm, 25 μm, or lower.

Example 4: Relationship Between Droplet Size and Peak Absorbance

Figure 22:
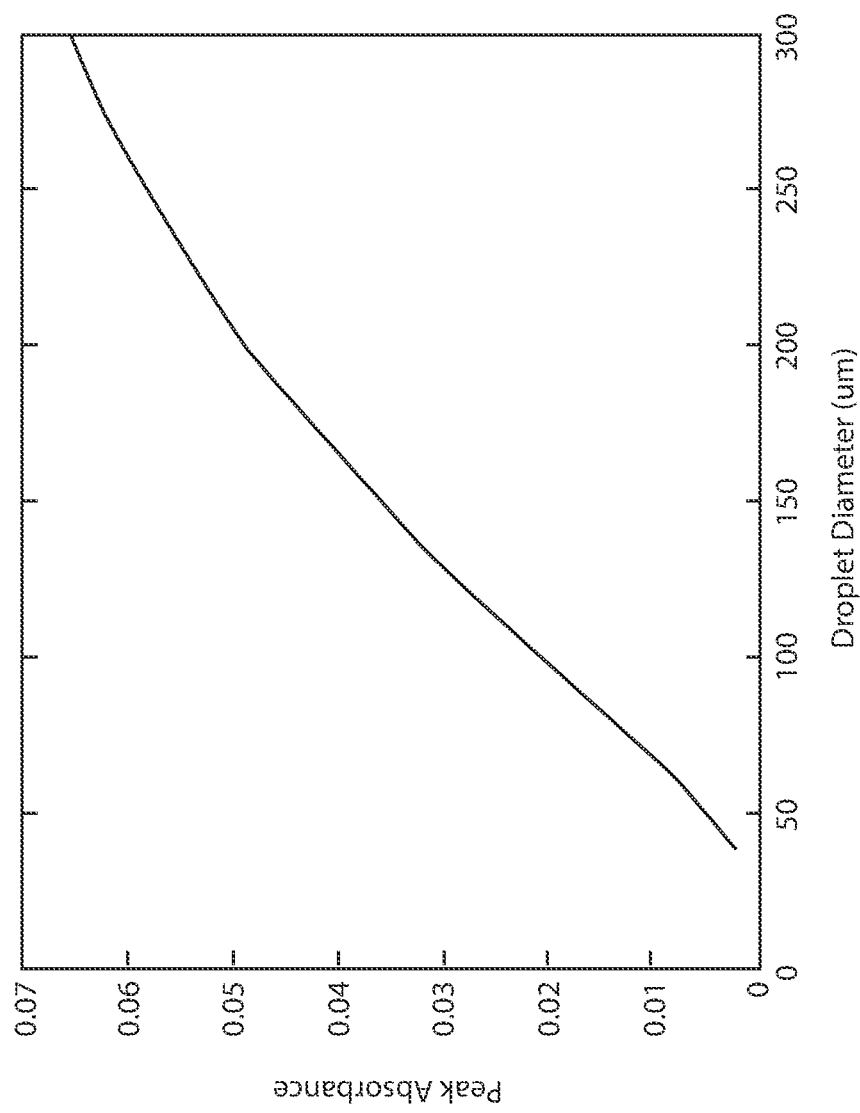
FIG. 22 is a graph showing the relationship between peak absorbance and droplet diameter.

With an established limit of detection (using that calculated in example 3, as merely one example), peak intensity can be correlated with droplet size using histogram data. The result is shown in FIG. 22 and shows a substantially linear relationship between droplet size and peak absorbance. This particular calibration is for the specific sensor tested. However, other individual sensors can be calibrated based on their air, water, and hexane-filled channel signals. Further, the relationship shown in FIG. 22 is for an aggregate of data. When a smaller individual droplet goes through the sensor it can give different sensor responses depending on the transit location within the channel. However, once the number of peaks detected is in the hundreds or larger the derived relationship between droplet size and peak absorbance can be used to determine a droplet distribution and concentration.

Example 5: Distinguishing Air Bubbles from Water Droplets

A water in fuel sensing system was set up consistent with that shown in FIG. 3 and as described in example 2. The sensor was placed on a fuel-water separation test bench typically used for testing water removal filters according to standard methods. In one instance, the system was set up such that water droplets (d50=75 μm, 500 ppm) would be received by the sensor. In another instance, the system was set up such that air bubbles would be received by the sensor. The main flow operated at 3 L/min and consisted of diesel fuel. Signal data was captured with a data acquisition system. Signal processing and peak identification was completed in MATLAB using standard peak fitting algorithms.

Figure 26:
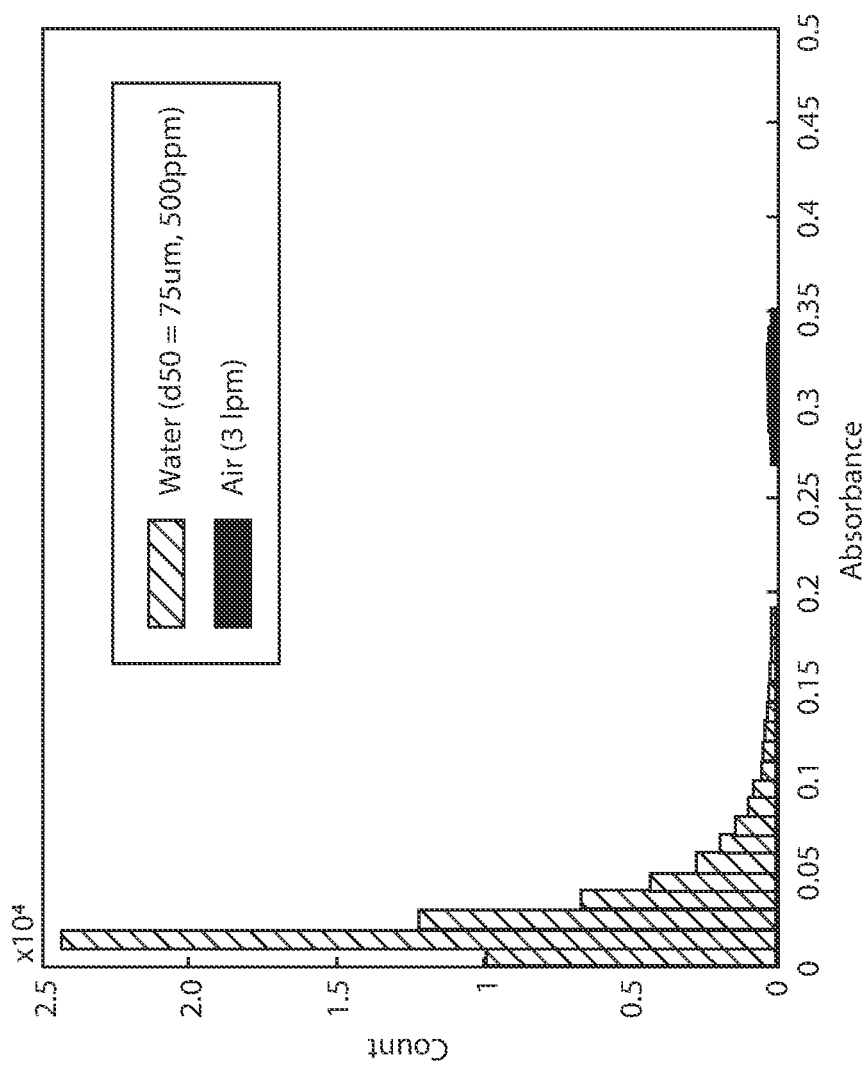
FIG. 26 is a histogram showing counts of peaks at different absorbance levels for water droplets and air bubbles in a system herein.
Figure 27:
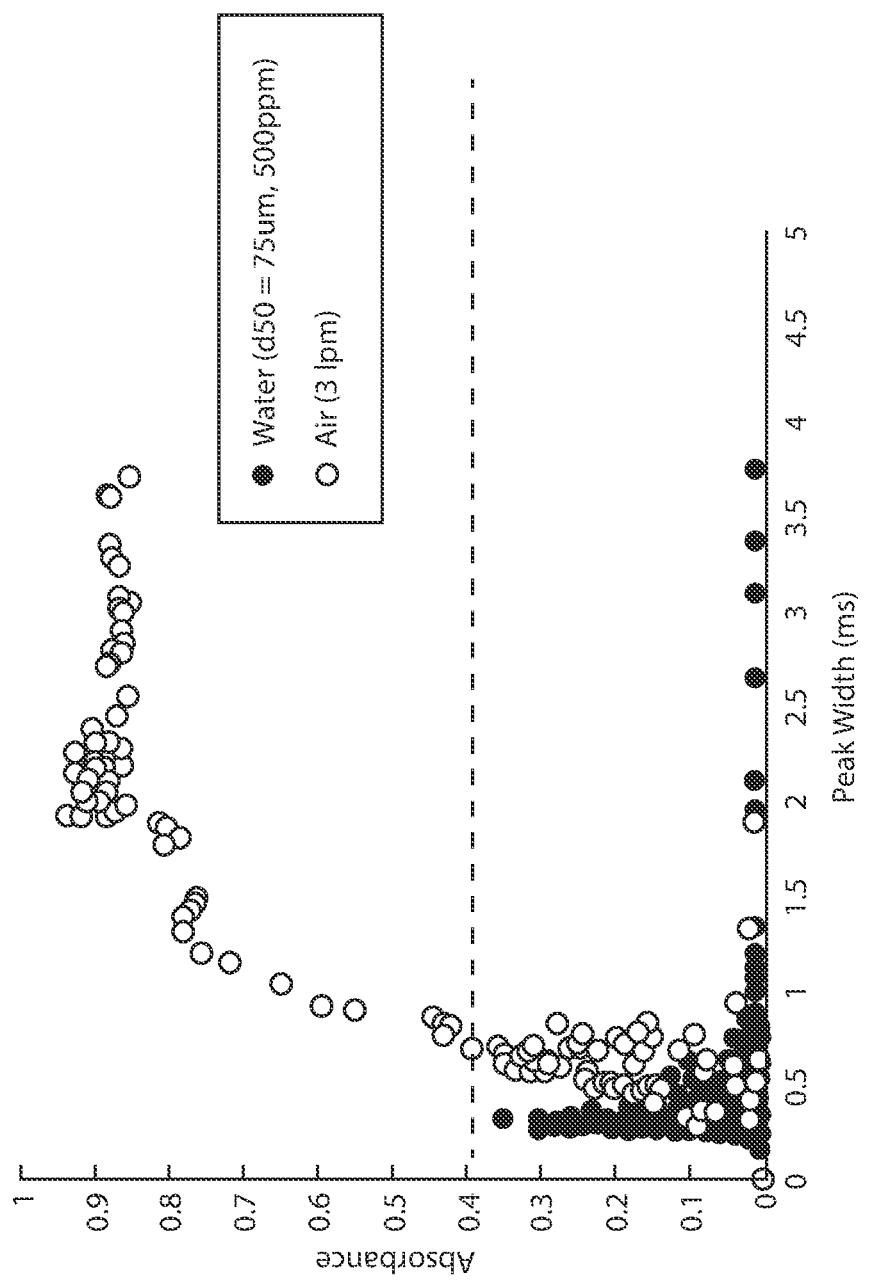
FIG. 27 is a graph showing the relationship between absorbance and peak width for water droplets and air bubbles in a system herein.

In FIG. 26, a histogram is shown of the counts of peaks at different absorbance levels for 15 minutes of data through the test system. It can be seen that the distribution of air peaks generated substantially larger absorbance values than did water droplets. Similarly, referring to FIG. 27, a graph showing the relationship between absorbance and peak width is shown for 30 seconds of data. It can be seen that the air bubbles generated substantially larger peak widths on average than the water droplets. This example shows that air bubbles generate absorbance peaks that are substantially different than water droplets. As such, systems herein can be configured to distinguish between water droplets and air bubbles and exclude the impact of air bubbles while measuring water concentration in fuel.

It should be noted that, as used in this specification and the appended claims, the singular forms "a," "an," and "the"

include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A water in fuel sensing system comprising:
   a light source;
   a light detector; and
   a sensor controller;
   wherein the sensor controller is in signal communication with the light detector;
   wherein the sensor controller is configured to
      evaluate signals received from the light detector, the signals comprising an absorbance peak;
      distinguish between air bubbles and water droplets based on a peak width of the absorbance peak received from the light detector;
      record information regarding the water droplets; and
      generate an estimate of an amount of water in a fuel.

2. The water in fuel sensing system of claim 1, wherein the sensor controller is configured to distinguish between air bubbles and water droplets based on a ratio of peak magnitude of the absorbance peak to peak width of the absorbance peak.

3. The water in fuel sensing system of claim 1, wherein the sensor controller is configured to distinguish between air bubbles and water droplets based on peak magnitude of the absorbance peak.

4. The water in fuel sensing system of claim 1, wherein the sensor controller is configured to distinguish between air bubbles and water droplets based on a magnitude of a reflection peak prior to the absorbance peak.

5. The water in fuel sensing system of claim 1, wherein the water in fuel sensing system is an on-vehicle sensing system.

6. The water in fuel sensing system of claim 1, further comprising a sampling channel, wherein the sampling channel is in fluid communication with a fuel line of a vehicle.

7. The water in fuel sensing system of claim 1, wherein the water in fuel sensing system is configured to generate the estimate of the amount of water in the fuel based on an estimated size of water droplets and an estimated number of water droplets.

8. The water in fuel sensing system of claim 1, wherein the light source is configured to emit near-infrared light.

9. The water in fuel sensing system of claim 1, wherein the water in fuel sensing system is configured to receive information regarding a fuel level within a fuel tank and cross-reference the fuel level information against recorded information regarding detected water droplets.

10. The water in fuel sensing system of claim 1, wherein the water in fuel sensing system is configured to generate recommendations for a vehicle driver based on detected water droplets, wherein the recommendations include at least one of a recommended refueling location, a recommended filter type, a recommended refueling time, and a recommended vehicle service.

11. The water in fuel sensing system of claim 1, wherein the sensor controller is configured to estimate a size of identified water droplets based in part on an increase and a successive decrease in the light received by the light detector with respect to a baseline level.

12. A water in fuel sensing system comprising:
   a light source;
   a first light detector;
   a second light detector; and
   a sensor controller;
   wherein the sensor controller is in signal communication with the first light detector and the second light detector;
   wherein the sensor controller is configured to
      evaluate signals received from the first light detector and the second light detector, the signals comprising an absorbance peak;
      distinguish between air bubbles and water droplets based on a peak width of the absorbance peak received from the first light detector;
      record information regarding the water droplets; and
      generate an estimate of an amount of water in a fuel.

13. The water in fuel sensing system of claim 12,
   wherein the first light detector is positioned to detect absorbance of light by a fluid passing through the water in fuel sensing system; and
   wherein the second light detector is positioned to detect reflection of light from bubbles within the fluid passing through the water in fuel sensing system.

14. The water in fuel sensing system of claim 12, wherein the sensor controller is configured to distinguish between air bubbles and water droplets based on a magnitude of a reflection peak prior to the absorbance peak.

15. A water in fuel sensing system comprising:
   a first light source, wherein the first light source is configured to emit near-infrared light;
   a second light source, wherein the second light source is configured to emit light within the visible spectrum;

a first light detector, wherein the first light detector is configured to detect light emitted from the first light source after it has passed through a fuel;
a second light detector, wherein the second light detector is configured to detect light emitted from the second light source after it has passed through the fuel; and
a sensor controller;
wherein the sensor controller is in signal communication with the first light detector and the second light detector;
wherein the sensor controller is configured to
evaluate signals received from the first light detector and the second light detector, the signals comprising an absorbance peak;
distinguish between air bubbles and water droplets based on a peak width of the absorbance peak received from the first light detector;
record information regarding the water droplets; and
generate an estimate of an amount of water in a fuel.

16. The water in fuel sensing system of claim 15, wherein the water in fuel sensing system is an on-vehicle sensing system.

17. The water in fuel sensing system of claim 15, further comprising a sampling channel, wherein the sampling channel is in fluid communication with a fuel line of a vehicle.

18. The water in fuel sensing system of claim 17, wherein the first light source and the second light source are configured to emit light into the sampling channel.

19. The water in fuel sensing system of claim 15, wherein the water in fuel sensing system is configured to generate the estimate of the amount of water in the fuel based on an estimated size of water droplets and an estimated number of water droplets.

* * * * *